US008258119B2

(12) United States Patent  
Gokaraju et al.

(10) Patent No.: US 8,258,119 B2
(45) Date of Patent: Sep. 4, 2012

(54) ANTI-CANCER DRUGS AND USES RELATING THERETO FOR METASTATIC MALIGNANT MELANOMA AND OTHER CANCERS

(75) Inventors: Ganga Raju Gokaraju, Andhra Pradesh (IN); Sudhakar Kasina, Mercer Island, WA (US); Rama Raju Gokaraju, Andhra Pradesh (IN); Trimurtulu Golakoti, Andhra Pradesh (IN); Venkateswarlu Somepalli, Andhra Pradesh (IN); Sengupta Krishanu, Andhra Pradesh (IN); Kiran Bhupathiraju, Andhra Pradesh (IN)

(73) Assignee: Kasina Laila Innova Pharmaceuticals, Vijayawada (IN)

( * ) Notice: Subject to any disclaimer, the term of this patent is extended or adjusted under 35 U.S.C. 154(b) by 142 days.

(21) Appl. No.: 12/559,811

(22) Filed: Sep. 15, 2009

(65) Prior Publication Data

US 2010/0068178 A1   Mar. 18, 2010

(30) Foreign Application Priority Data

Sep. 15, 2008  (IN) .......................... 2230/CHE/2008

(51) Int. Cl.
 C07D 333/38 (2006.01)
 C07D 495/04 (2006.01)
 A61K 31/655 (2006.01)
 A61K 31/53 (2006.01)
 A61P 35/00 (2006.01)

(52) U.S. Cl. ........ 514/151; 514/243; 534/551; 544/183; 544/184

(58) Field of Classification Search .................. None
 See application file for complete search history.

(56) References Cited

FOREIGN PATENT DOCUMENTS

| DE | 1020641 | 12/1957 |
|---|---|---|
| DE | 1945430 | 3/1970 |
| GB | 1288067 | 9/1972 |

OTHER PUBLICATIONS

Zhu, Lianjie et al, "A Class of Fluorescent Heterocyclic Dyes Revisited: Photophysics, Structure, and Solvent Effects", Spectrochimica Acta Part A: Molecular and Biomolecular Spectroscopy, 73(4), 757-763, Aug. 15, 2009.*
Henriksen, L. et al., Chemical Abstracts, 78:43433, 1973, "Chemistry of 1,1-Diothiolates. 2. Thieno-1,2,3-Triazines by Diazotization of 3-Aminothiophene-2- and -4-Carboxamides", Acta Chemica Scandinavica, (1947-1973) (1972), 26(8), 3342-3346.*
Golub et al., Science, 286, 531-537, Oct. 1999.*
Fitzpatrick, T.B., et al., Sunlight and skin cancer. N. Engl. J. Med., 1985, 313, 818-820.
Pathak, M.A., et al., Photobiology of melanin pigmentation: dose/response of skin to sunlight and its contents. J. Am. Acad. Dermatol., 1983, 9, 724-733.
Riley, P.A., Melanin. Int. J. Biochem. Cell Biol., 1997, 29, 1235-1239.
Rutao, C., et al., Central Role of Central Role of p53 in the Suntan Response and Pathologic Hyperpigmentation, Cell, 2007, 128, 853-864.
Oren., et al.,. The Sunny Side of p53, Cell, Mar. 9, 2007, 128, 826-828.
Danson, S.J., et al., Temozolomide: a novel oral alkylating agent. Expert Rev. Anticancer.
Nagasubramanian, R., et al., Tomozolamide: Realizing the promise and potential. Curr. Opin. Oncol., 2003, 15, 412-418.
Lanzetta, G., et al., Temozolomide in radio-chemotherapy combined treatment for newly-diagnosed glioblastoma multi-forme: Phase—II clinical trial. Anticancer Res., 2003, 23, 5159-5164.
Stupp, R., et al., Radiotherapy plus concomitant and adjuvant temozolomide for glioblastoma. N. Engl. J. Med., 2005, 352, 987-996.
Gilbert, M.R., et al., Advances in the treatment of brain tumors: dawn of a new era? Curr. Oncol. Rep., 2006, 8, 45-49.
Atallah, E., et al., Treatment of metastatic malignant melanoma. Curr. Treat. Options Oncol., 2005, 6, 185-193.
Panetta, J.C et al., Population of temezolomide and metabolites in infants and children with primary central nervous system tumors. Cancer Chemother. Pharmacol., 2003, 52, 435-441.
Houghton, P.J., et al., Anti-tumor activity of tomozolomide combined with irinotecan is partly independent of O6—methylguanine—DNA methyltransferase and mismatch repair phenotypes in xenograft models. Clin. Cancer Res., 2000, 6, 4110-4118.
Middlemas, D.S., et al.,. Biochemical correlates of temozolomide sensitivity in pediatric solid tumor xenograft models. Clin. Cancer Res., 2000, 6, 998-1007.
Aksoy, S., et al., Successful treatment of a chemoresistant tumor with temozolomide in an adult patient: report of a recurrent intracranial mesenchymal chondrosarcoma. J. Neurooncol., 2005, 71, 333-334.
Patel, V.J., et al., Schedule-dependent activity of temozolomide plus CPT-11 against a human central nervous system tumor-derived xenograft. Clin. Cancer Res., 2000, 6, 4154-4157.
Anderson, P.M., et al., Novel therapeutic approaches in pediatric and young adult sarcoma. Curr. Oncol. Rep., 2006, 8, 310-315.
Wagner, L.M., et al., Temozolomide and intravenous irinotecan notecan for treatment of advanced Ewing's sarcoma. Pediatr. Blood Cancer, 2007, 48, 132-139.
Wagner, L.M., et al., Phase I trial of temozolomide and protracted irinotecan in pediatric patients with refractory solid tumors. Clin. Cancer Res., 2004, 10, 840-848.

(Continued)

*Primary Examiner* — Fiona T Powers
(74) *Attorney, Agent, or Firm* — Kramer & Amado, P.C.

(57) ABSTRACT

The present invention discloses triazene analogs of the general formula (I) and formula (II), their tautomeric forms, stereoisomers, polymorphs, hydrates, solvates, and pharmaceutically acceptable salts thereof for the metastatic malignant melanoma and other cancers including but not limited to lymphomas, sarcomas, carcinomas, and gliomas.
The invention further discloses a process for the preparation of the above said triazene analogs of formula (I) and formula (II), and their pharmaceutically acceptable compositions.

32 Claims, 10 Drawing Sheets

OTHER PUBLICATIONS

Kushner, B.H., et al., Irinotecan plus temozolomide for relapsed or refractory neuroblastoma. J. Clin. Oncol., 2006, 24, 5271-5276.

De Angulo, G., et al., Early lymphocyte recovery as a prognostic indicator for High-risk Ewing's sarcoma. J. Pediatr. Hematol. Oncol., 2007, 29, 48-52.

Dubois, S.G., et al., Early lymphocyte recovery in Ewing sarcoma. J. Pediatr. Hematol. Oncol., 2007, 29, 351-352.

Losa, R., et al., Phase II study with the combination of gemcitabine and DTIC in patients with advanced soft tissue sarcoma. Cancer Chemother. Pharmacol., 2007, 59, 251-259.

Awada, A., et al., Prolonged schedule of temozolomide (Temodal) plus liposomal doxorubicin (Caelyx) in advanced solid cancers. Anti-cancer Drugs, 2004, 15, 499-502.

Cruz-Munoz, W., et al., Effective treatment of Advanced human melanoma metastases in immunodefficient mice using combination metronomic chemotherapy regimens. Clin. Cancer Res., 2009, 15, 4867-74.

Ott, P.A., et al., Phase II trial of dacarbazine and thalidomide for the treatment of malignant melanoma. Chemotherapy, 2009, 55, 221-7.

Tagne, J.B., et al., Nanoemulsion preparations of the anticancer drug dacarbazine significantly increase its efficacy in a xenograft mouse melanoma model. Mol. Pharm., 2008, 5, 1055-63.

Mansfield, A.S., et al., Novel therapeutics for the treatment of metastatic melanoma. Future Oncol., 2009, 5, 543-57.

Lui, P., et al., Treatments for metastatic melanoma: synthesis of evidence from randomized trials. Cancer Treat. Rev., 2007, 33, 665-80.

Hartmann, H., et al., A simple method for the synthesis of 5-aryl-3-aminoalkoxycarbonylthiophenes. Synthesis, 1984, 275-276.

Shishoo, C.J et al., Synthesis of some 2-substituted-6-phenyl- and 7-phenyl-thieno[3,2-d]pyrimidin-4(3H)-ones. Indian J. Chem., 1994, 33B, 436-440.

Barker, J.M., et al., A rapid conversion of 3-oxothiolanes into 3-aminothiolanes. Synth. Commun., 2002, 32, 2565-2568.

Dowd, P., et al., Free radical ring-expansion leading to novel six- and seven membered heterocycles. Tetrahedron, 1991, 47, 4847-4860.

Woodward, R.B., et al., Tetrahydrothiophene derivatives. J. Am. Chem. Soc., 1946, 68, 2229-2235.

Hesse, S., et al., Microwave-assisted synthesis of 2-aminothiophene-3-carboxylic acid derivatives, 3H-thieno[2,3-d] pyrimidin-4-one and 4-chlorothieno[2,3-d]pyrimidine. Tetrahedron Letts., 2007, 48, 5261-5264.

Dumaitre, B., et al., Synthesis and cyclic GMP phosphodiesterase inhibitory activity of a series of 6-phenylpyrazolo [3,4-d]pyrimidones. J. Med. Chem., 1996, 39, 1635-1644.

Banerjee, S., et al., VEGF-A165 induces human aortic smooth muscle cell migration by activating neuropilin-1-VEGFR1-PI3K axis. Biochemistry, 2008, 47, 3345-51.

Tewari, M., et al., Yama/CPP32B, a mammalian homolog of CED-3, is a CrmA-inhibitable protease that cleaves the death substrate poly(ADP-ribose) polymerase. Cell, 1995, 81, 801-809.

Sengupta, K., et al., WISP-2/CCN5 is involved as a novel signaling intermediate in Phorbol ester protein kinase Calpha-mediated breast tumor cell proliferation. Biochemistry, 2006, 45, 10698-709.

Wu, et al., Inhibitory effects of apigenin on the growth of gastric carcinoma SGC-7901 cells. World. J. Gastroenterol, 2005, 11, 4461-4464.

Ray, G., et al., Modulation of cell-cycle regulatory signaling network by 2-Methoxyestradiol in prostate cancer cells is mediated through multiple signal transduction pathways. Biochemistry, 2006, 45, 3703-3713.

Sengupta, K., et al., Thombospondin-1 Disrupts Estrogen-Induced Endothelial Cell Proliferation and Migration and its Expression Suppressed by Estradiol. Mol. Cancer Res., 2004, 2, 150-158.

Chalupowicz, et al., Fibrin II Induces Endothelial Cell Capillary Tube Formation. J. Cell Biol., 1995, 130, 207-215.

Rose., et al., Dietary glycine inhibits the growth of B16 melanoma tumors in mice. Carcinogenesis, 1999, 20, 793-798.

International Search Report dated Mar. 18, 2010 issued for PCT/IN2009/000504 (WO2010/029577).

Henriksen et al., "The Chemistry of 1, 1-Dithiolates. 2. Thieno-1,2,3-triazines by Diazotation of 3-Amino-thiophene-2- and 4 carboxamides". Acta Scandinavica vo. 26, No. 8, 1972, pp. 3342-3346.

Wagner et al., "Synthesis and Cystostatic Activity of 4-Substituted Derivatives of Isoxazolyltriazenes". Polish Journal of Chemistry, Polskie Towrzystwo Chemiczne, PL. vol. 77, No. 8, 2003, pp. 1001-1006.

Lowe et al., "Antitumor imidazotetrazines. 25. Crystal structure of 8-carbomoy1-3-methylimidazo[5,1-d]-1,2,3,5-tetrazine-4(3H)-one (temozolomide) and structural comparisons with related drugs mitozolomide and DTIC". Journal of Medicinal Chemistry, American Chemical Society, Washington, US, vol. 35, No. 18, Jan. 1, 1992, pp. 3377-3382.

Fulmer Shealy et al., "Synthesis, Antileukemic Activity, and Stability of 3-(Substituted-Triazeno)pyrazole-4-carboxylic Acid Esters and 3-(Substituted-Triazeno) pyrazole-4-carboxamides". Journal of Pharmaceutical Sciences, vo./ 60, No. 4, Apr. 1971 pp. 554-560.

Wayne Noell et al., "Pyrazoles. 4. Analogs of 3-(3,3-Dimethyl-1-triazeno)-pyrazole-4-carboxamide". Journal of Medicinal Chemistry. vol. 14, No. 12m 1971, pp. 1245-1246.

\* cited by examiner

Figure: 2

Figure 4
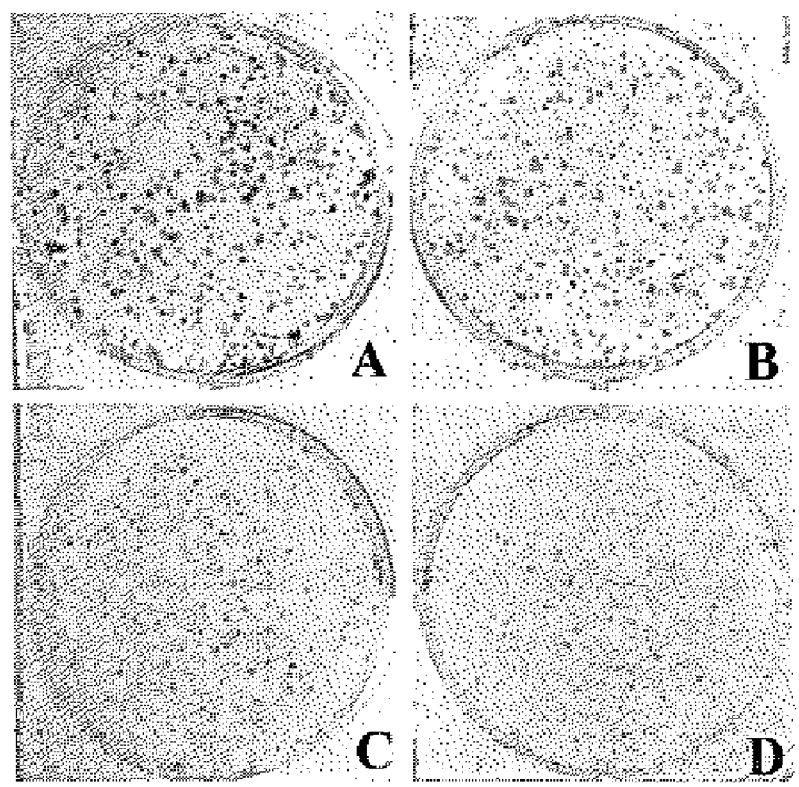
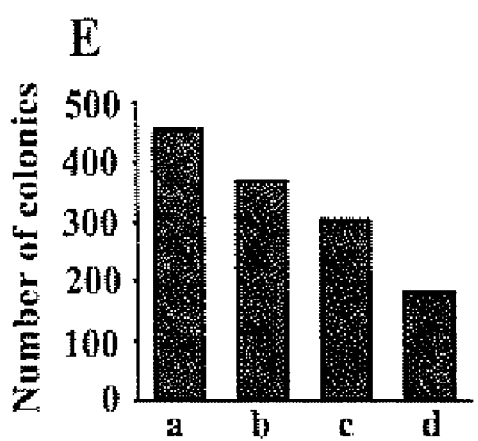
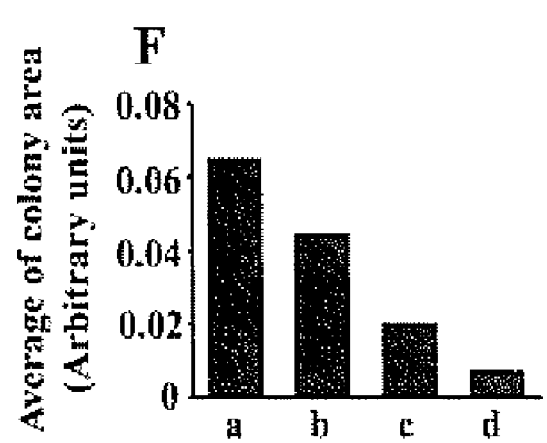

Figure: 8
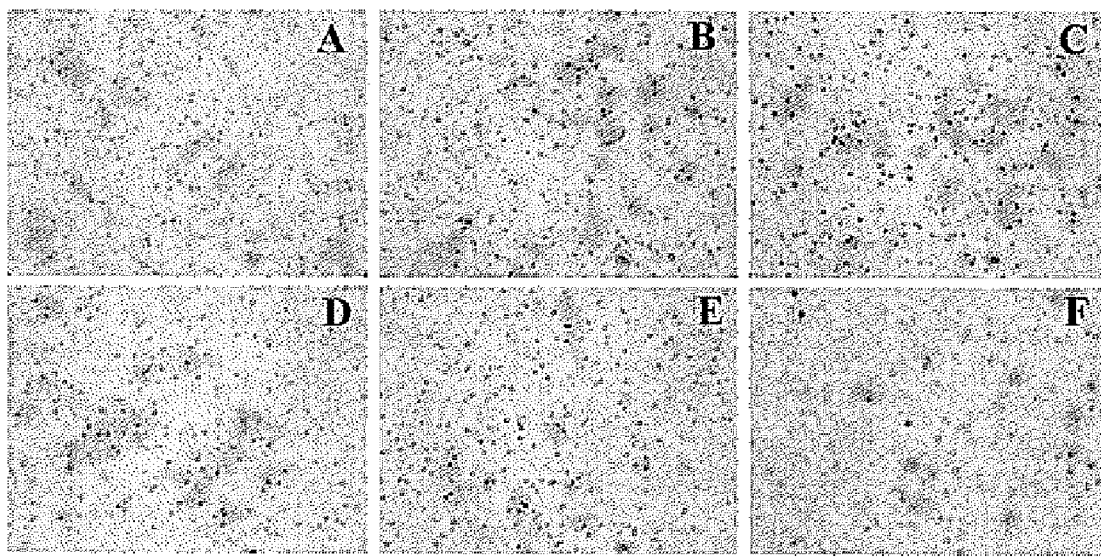
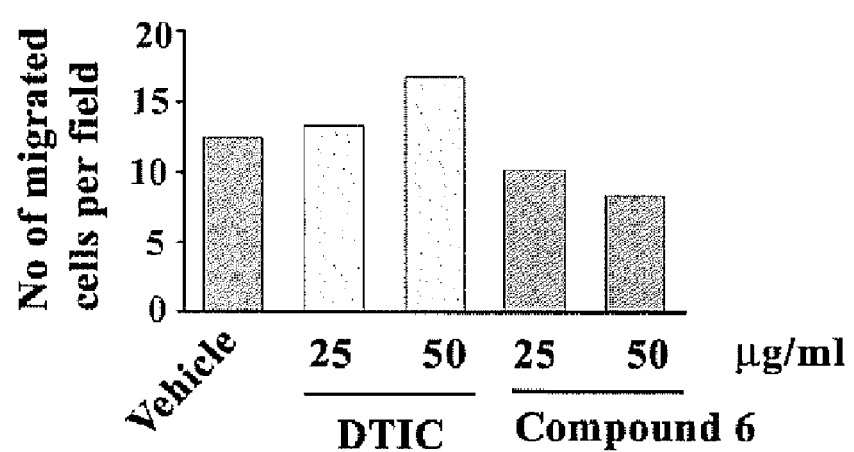

| Treatment Groups | Average tumor weight (gm) | SD | reduction wrt.control |
|---|---|---|---|
| Control | 2.858 | 0.865 | |
| DTIC 50 mg/kg | 2.046 | 0.232 | 28.411 |
| DTIC 100 mg/kg | 1.957 | 0.641 | 31.532 |
| Compound 6 (50 mg/kg) | 1.858 | 0.881 | 34.989 |
| Compound 6 (100 mg/kg) | 1.168 | 0.735 | 59.118 |

ANTI-CANCER DRUGS AND USES RELATING THERETO FOR METASTATIC MALIGNANT MELANOMA AND OTHER CANCERS

FIELD OF THE INVENTION

The present invention relates to triazene analogs of the general formula (I) and formula (II), their tautomeric forms, stereoisomers, polymorphs, hydrates, solvates, and pharmaceutically acceptable salts thereof for the metastatic malignant melanoma and other cancers including but not limited to lymphomas, sarcomas, carcinomas, and gliomas.

The present invention further relates to a process for the preparation of the above said triazene analogs of formula (I) and formula (II), and their pharmaceutically acceptable compositions.

BACKGROUND OF THE INVENTION

Melanoma, a malignant neoplasm, is derived from cells that are capable of forming melanin, arising most commonly in the skin of any part of the body and in the eye, or rarely, in the mucus membranes of the genitalia, anus, oral cavity, or other sites. It occurs mostly in adults and may originate de novo or from a pigmented nevus or lentigo maligna. In the early phases, the cutaneous form is characterized by a proliferation of cells at the dermal epidermal junction which soon invades adjacent tissues. The cells vary in amount and pigmentation of cytoplasm; the nuclei are relatively large and frequently bizarre in shape, with prominent acidophilic nucleoli; the mitotic figures tend to be numerous. Melanomas frequently metastasize widely; regional lymph nodes, skin, liver, lungs, and brain are likely to be involved.

In January 1985, the Environmental Protection Agency (EPA) predicted that depletion of the Earth's Ozone layer, which guards against ultraviolet (UV) radiation from space, would cause an increase in the number of skin cancer cases worldwide, including melanomas. The EPA estimated an annual increase of two million cases by the year 2050, when the ozone layer is expected to diminish by 10% because of human activities—primarily the release of long-lived Chlorofluorocarbons into the atmosphere (now banned in most developed countries). Public health efforts have focused on encouraging people to use sunscreen, avoid outdoor activities during peak exposure times, perform frequent self-checks of the skin, and visit dermatologists when irregularities are noted. Exposure to higher levels of ultraviolet radiation may also promote cataracts and immune system dysfunction.

UV radiation represents a definitive risk factor for skin cancer, especially when exposure occurs in combination with certain underlying genetic traits, such as red hair and fair skin (1). Pigmentation of the skin results from the synthesis of melanin in the pigment-producing cells, the melanocytes, followed by distribution and transport of pigment granules to neighboring keratinocytes. It is commonly believed that melanin is crucial for absorption of free radicals that have been generated within the cytoplasm by UV and acts as a direct shield from UV and visible light radiation (2, 3).

UV-induced pigmentation (sun tanning) requires induction of α-melanocyte-stimulating hormone (α-MSH) secretion by keratinocytes. α-MSH and other bioactive peptides are cleavage products of Pro-Opiomelanocortin (POMC) (4). The p53 tumor suppressor gene is one of the most frequent targets for genetic alterations in cancer. p53 is a transcriptional regulator of the POMC gene, which translates to proteins that cause the melanocytes to produce melanin, which wards off skin cancer by absorbing UV radiation. Direct mutational inactivation of p53 is observed in close to half of all human tumors (5).

Malignant melanoma is a skin cancer which is, by far, one of the hardest cancers to treat today. Dacarbazine (DTIC) is the only single agent used to treat metastatic malignant melanoma. However, in the clinical setting the Complete Response (CR) rate for Dacarbazine is below 10% and hence is an unmet medical need and there exists a need for better agents. In addition. Dacarbazine is also indicated for Hodgkin's lymphoma as a secondary line therapy when used in combination with other effective drugs. Chemically. DTIC is 5-(3,3-dimethyl-1-trizeno)-imidazole-4-carboxamide with the following structural formula:

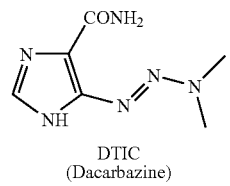

DTIC
(Dacarbazine)

Dacarbazine, however, requires bioactivation in vivo by the liver. One of the methyl groups of the dimethyltriazeno functionality is activated by liver microsomal enzymes and, in particular, by the Cytochrome P450, to oxidation, resulting in a hydroxymethyl group. Thus, the oxidative mono-demethylation of the dimethyltriazeno functionality affords monomethyltriazene. The monomethyltriazene metabolite, 3-methyl-(triazen-1-yl)-imidazole-4-carboxamide (MTIC) is further hydrolyzed to 5-amino-imidazole-4-carboxamide (AIC), which is known to be an intermediate in purine and nucleic acid biosynthesis and to methylhydrazine, which is believed to be the active alkylating species. The Cytochrome P450 enzymes play only a minor role in the metabolism of MTIC.

Temozolomide is also a similar imidazotetrazine alkylator that methylates DNA at nucleophilic site. Temozolomide is orally bioavailable, more lipophilic, and spontaneously converted to MTIC, and also seems to generate less nausea (6). The $O^6$-methylguanine adduct causes a mismatch during DNA replication and the addition of a thymidine, instead of cytosine, to the newly formed DNA strand (7). Because of the excellent CNS biodistribution, temozolomide has been useful as a radiosensitizer in both primary brain tumors and CNS metastases (8-11). The pharmacokinetics of temozolomide has been studied in children, and clearance is related to body surface area (12). Temozolomide improves quality of life when used with radiation in patients with brain metastases. Unlike Dacarbazine, Temozolomide has activity against sarcoma (13-15). Thus, it may be useful in sarcoma radiosensitization for primary control as well as for the treatment of metastases. Temozolomide is a radiosensitizer that is well tolerated and has modest side effects. The combination of Temozolomide and Irinotecan is more than additive against some cancers (16). The authors report that their experience confirms a high response rate in relapsed Ewing's sarcoma and DSRCT that is possibly even higher than that reported in the literature (17-19). The Temozolomide plus Irinotecan combination is less immune suppressive than standard cyclophosphamide-containing regimens (20). This might be especially important in Ewing's sarcoma since these authors and others have shown that lymphocyte recovery (i.e., absolute lymphocyte count >500 on day 15 after the first cycle of chemotherapy) is associated with significantly higher survival in Ewing's sarcoma (21, 22). Temozolomide or Dacarbazine has also been combined with other drugs including Gemcitabine and Doxorubicin liposomes (23, 24). The disappearance of DTIC from the plasma is biphasic with an initial half life of 19 minutes and a terminal half life of five hours. In a patient with renal and hepatic dysfunctions, the half lives were lengthened to 55 minutes and 7.2 hours, respectively. The average cumulative excretion of unchanged DTIC in the urine is 40% of the injected dose in six hours. DTIC is subject to renal tubular secretion rather than Glomerular Filtration. At therapeutic concentrations, DTIC is not appreciably bound to human plasma protein.

In humans, DTIC is extensively degraded. Besides unchanged DTIC, AIC is a major metabolite of DTIC excreted in the urine. Although the exact mechanism of action of DTIC is not known, three hypotheses have been offered:

1. Inhibition of DNA synthesis by acting as a purine analog
2. Acting as an alkylating agent
3. Interaction with SH groups Thus, the biochemical mechanism of action of the resulting MTIC reactive species whose cytotoxicity involved generation of methyl carbonium ion in vivo is thought to be primarily due to alkylation of DNA. Alkylation (methylation) occurs mainly at the $O^6$ and $N^7$ positions of guanine.

Alternatively, DTIC, prior to its metabolism to the monomethyltriazene, is oxidized initially to monohydroxymethyl and finally to an aldehyde. The monomethyltriazene, in its aldehyde form prior to oxidative monodemethylation, is cyclized to the cyclic compound (as shown in Scheme 1) which interferes with the double helix DNA structure and blocks replication of the cancer cells. And finally, the secondary metabolite, AIC, is inactive.

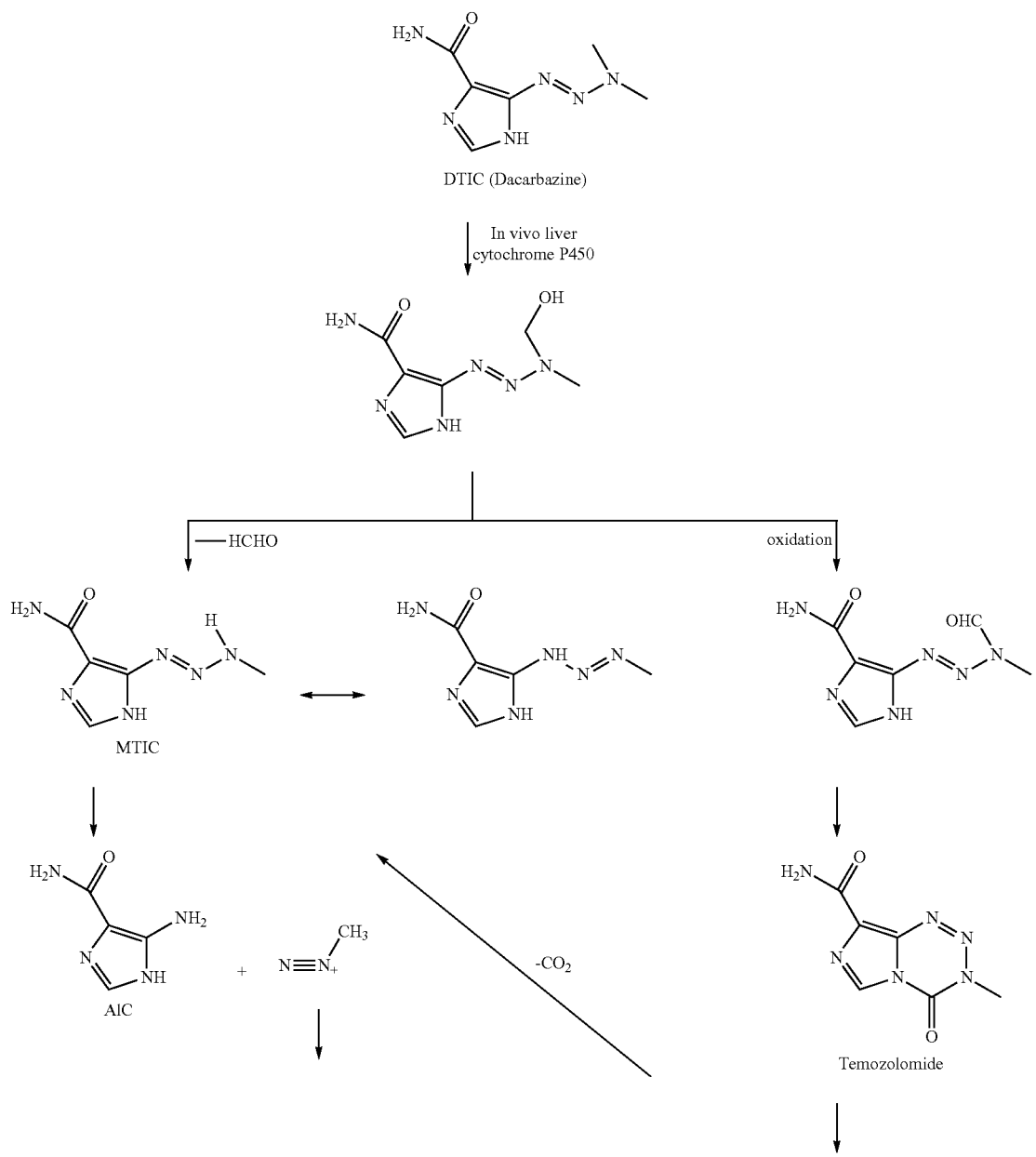

Scheme 1. Biochemical mechanism of action of Dacarbazine

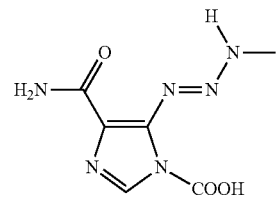

The imidazole ring system of the Dacarbazine is hydrophilic in nature. Therefore, there is a need in the art for possibly effective binding to the melanin such that the cytotoxic functionality of the molecule is one hundred percent effective. Thus, the present inventors have aimed to provide novel compounds with increased lipophilicity thereby providing more target specificity. Thus, Thiophene, which has a five-membered heterocyclic ring system, is lipophilic in nature and may have effective binding by increased avidity to the melanin, as a result, one would be able to get the same therapeutic effectiveness at a significantly lower dose, hence minimizing the toxicity. This would in turn afford high specificity with a larger window of the Therapeutic Index (TI). In general, for the treatment of cancer patients, a larger therapeutic index is preferred. This is because, one would like to start the therapeutic regimen with a very high Maximum Tolerated Dose (MTD) such that the cancer cells would be hit hard in the first chemotherapy itself. Otherwise, the surviving cancer cells would repair the DNA damage and subsequently metastasize to the other organs. In addition, the cancer cells that survived from the first treatment would become resistant to the second chemotherapy again, if needed. And besides, due to weakness of the immune system from the first chemotherapy, a suboptimal dose would be given in the second treatment that would contribute to toxicity.

As shown in scheme-1, unlike DTIC, better interaction of the thiophene ring system with the SH groups on the surface of the tumor antigen results in increased efficacy. This is because of sulfur (S) being larger atom and hence a five membered heterocyclic aromatic thiophene ring system resemble a phenyl ring in space, would contribute it's loan pair of electrons to the rest of the ring for better interaction with sulfhydryls at the tumor site. In addition, due to it's electronic configuration, the heterocyclic aromatic thiophene ring system may be superior over DTIC by way of inhibition of DNA synthesis by acting as a purine analog as well as acting as an alkylating agent. Also, unlike DTIC, while Amino Imidazole Carboxamide (AIC) is inactive, the corresponding Amino Thiophene Carboxamide (ATC) would very well be active in vivo via de-localization of electrons from the ring sulfur for increased efficacy. Thus, the novel triazeno thiophene analogs have several additional advantages inherently built in within the structure over dacarbazine for increased activity.

In addition to its biochemical mechanism of action, recently there are several reports in the literature for significantly increasing the efficacy of Dacarbazine by using it in combination with other chemotherapeutic agents (25, 26). Likewise, in a pre-clinical setting, nanoemulsion preparations of Dacarbazine in a xenograft mouse melanoma model has been used to significantly increase it's efficacy (27). Similarly, a number of innovative therapeutic strategies have been pursued in order to improve the outcomes, including immune therapy, tyrosine kinase inhibitors and angiogenesis inhibitors (28). The literature reports treatment for metastatic melanoma using Dacarbazine in combination with interferons is poor (29). As described above, currently, dacarbazine and temozolamide have been extensively used chemotherapeutic agents for treating metastatic malignant melanoma. However, the success rate is low and the side effects are high. Hence, there exists an unmet medical need for the development of effective agents and approaches for treatment of metastatic malignant melanoma remains an immense challenge.

SUMMARY OF THE INVENTION

The present invention provides compounds of the formula (I), designated herein as 'triazene analogs'.

General formula I

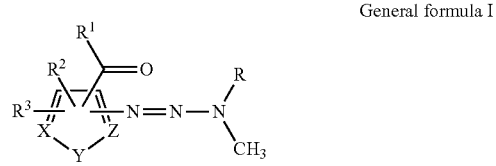

Wherein,
R is independently selected from H, $CH_3$, $CH_2OH$
$R^1$ is independently selected from OH, $NHR^4$, $NR^4R^5$, SH
At least one of $R^2$, and $R^3$ is selected from H, $N=N-N(CH_3)_2$, $N=N-NHCH_3$, $N=N-N(CH_3)CH_2OH$, $CONHR^4$, $CONR^4R^5$, $CONHNH_2$, $CONHNHR^4$, $CONHNR^4R^5$, $COOCH_3$, $COOCH_2CH_3$, COOH, COSH, CN, $C\equiv CH$, $SO_2NH_2$, $SO_2NHR^4$, $SO_2NR^4R^5$, $SO_3H$, $SO_2CH_3$, $SO_2CH_2CH_2NH_2$, $NHCH_2COOH$, $NHCH(CH_3)COOH$, $NO_2$, $CF_3$, Cl, Br, F, I, $CCl_3$, Ph ($C_6H_5$), $CH_3$, $C_2H_5$, n-$C_3H_7$, iso-$C_3H_7$, n-$C_4H_9$, iso-$C_4H_9$, tert-$C_4H_9$, OH, $OCH_3$, $NH_2$, $NHCH_3$, etc. electron withdrawing and electron donating groups.
$R^4$ and $R^5$ are independently selected from H, $C_1$-$C_{10}$ alkyl, alkenyl, alkylol, alkylamine, etc.
X, Y, and Z are independently selected from C, N, O, and S such that the resulting five membered ring systems of the heterocyclic aromatic moieties are un-substituted and substituted thiophene, furan, thiazole, isothiazole, and furazole.

In another aspect, the present invention also provides compounds of the formula (II)

General formula II

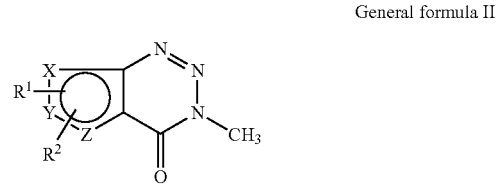

At least one of $R^1$, and $R^2$ is independently selected from H, $N=N-N(CH_3)_2$, $N=N-NHCH_3$, $N=N-N(CH_3)CH_2OH$, $CONH_2$, $CONHR^4$, $CONR^4R^5$, $CONHNH_2$, $CONHNHR^4$, $CONHNR^4R^5$, $COOCH_3$, $COOCH_2CH_3$, COOH, COSH, CN, $C\equiv CH$, $SO_2NH_2$, $SO_2NHR^4$, $SO_2NR^4R^5$, $SO_3H$, $SO_2CH_3$, $SO_2CH_2CH_2NH_2$, $NHCH_2COOH$, $NHCH(CH_3)COOH$, $NO_2$, $CF_3$, Cl, Br, F, I, $CCl_3$, Ph ($C_6H_5$), $CH_3$, $C_2H_5$, n-$C_3H_7$, iso-$C_3H_7$, n-$C_4H_9$, iso-$C_4H_9$, tert-$C_4H_9$, OH, $OCH_3$, $NH_2$, $NHCH_3$, etc. electron withdrawing and electron donating groups.

$R^4$ and $R^5$ are independently selected from H, $C_1$-$C_{10}$ alkyl, alkenyl, alkylol, alkylamine, etc.

X, Y, and Z are independently selected from C, N, O, and S such that the heterocyclic aromatic five membered ring of the fused bicyclic systems are un-substituted and substituted thiophene, furan, thiazole, isothiazole, and furazole. The compound of general formula (II) is not 3-methylthiopheno [3,2-d]1,2,3-triazin-4-one (X=Y=C; Z=S; $R^1$=$R^2$=H).

In another aspect, the present invention encompasses pharmaceutically acceptable salts of the compounds of the formula (I) and (II), for example organic or inorganic acid addition salts.

In another aspect, the present invention provides compositions comprising at least one triazene analog of formula (I) and/or formula (II) or pharmaceutically acceptable salts thereof and pharmaceutically acceptable carrier or diluents.

In another aspect, the present invention provides compositions comprising at least one triazene analog of formula (I) and/or formula (II) or pharmaceutically acceptable salts thereof and at lest one chemotherapeutic agent and optionally pharmaceutically acceptable carrier or diluents.

In another aspect, the present invention provides compositions comprising triazene analogs of formula (I) and/or formula (II) or pharmaceutically acceptable salts thereof and at lest one chemotherapeutic agent and at least one biologic response modifying agent and optionally pharmaceutically acceptable carrier or diluents.

In another aspect, the present invention provides a method of inhibiting cancer cell growth or killing a cancer cell in a patient by administering to a subject in need thereof, in an amount that is effective to kill a cancer cell, of a triazene analog of formula (I) and/or formula (II) or compositions containing the same or in combination with other chemotherapeutic agents thereof.

DESCRIPTION OF THE DRAWINGS

FIG. 4 represents images showing inhibition of B16F0 colony formation in presence of DTIC and Compound 6 in vitro. B16F0 cells were treated with either 0.1% DMSO (A), or 100 µg/ml of DTIC (B) or 50 µg/ml (C) or 100 µg/ml (D) of Compound 6. The average number of colonies and the average area of colonies in 0.1% DMSO (a), or 100 µg/ml of DTIC (b) or 50 µg/ml of compound 6 (c) or 100 µg/ml of compound 6 (d) treated cultures are represented in bar diagrams E and F, respectively.

FIG. 8 shows inhibitory effect of Compound 6 on human endothelial cell migration. Microphotographs illustrate the migration of HUVECs in the presence of either DTIC (25 and 50 µg/ml at panels B and C, respectively) or Compound 6 (25 and 50 µg/ml at panel E and F, respectively). Panels A and D represent cellular migration in 0.1% DMSO treated vehicle control wells. The bar graph shows the number of migrated cells under different culture conditions as indicated under each bar. Each bar represents mean of migrated cells calculated from at least twenty fields under 20× objective.

Figure 1:
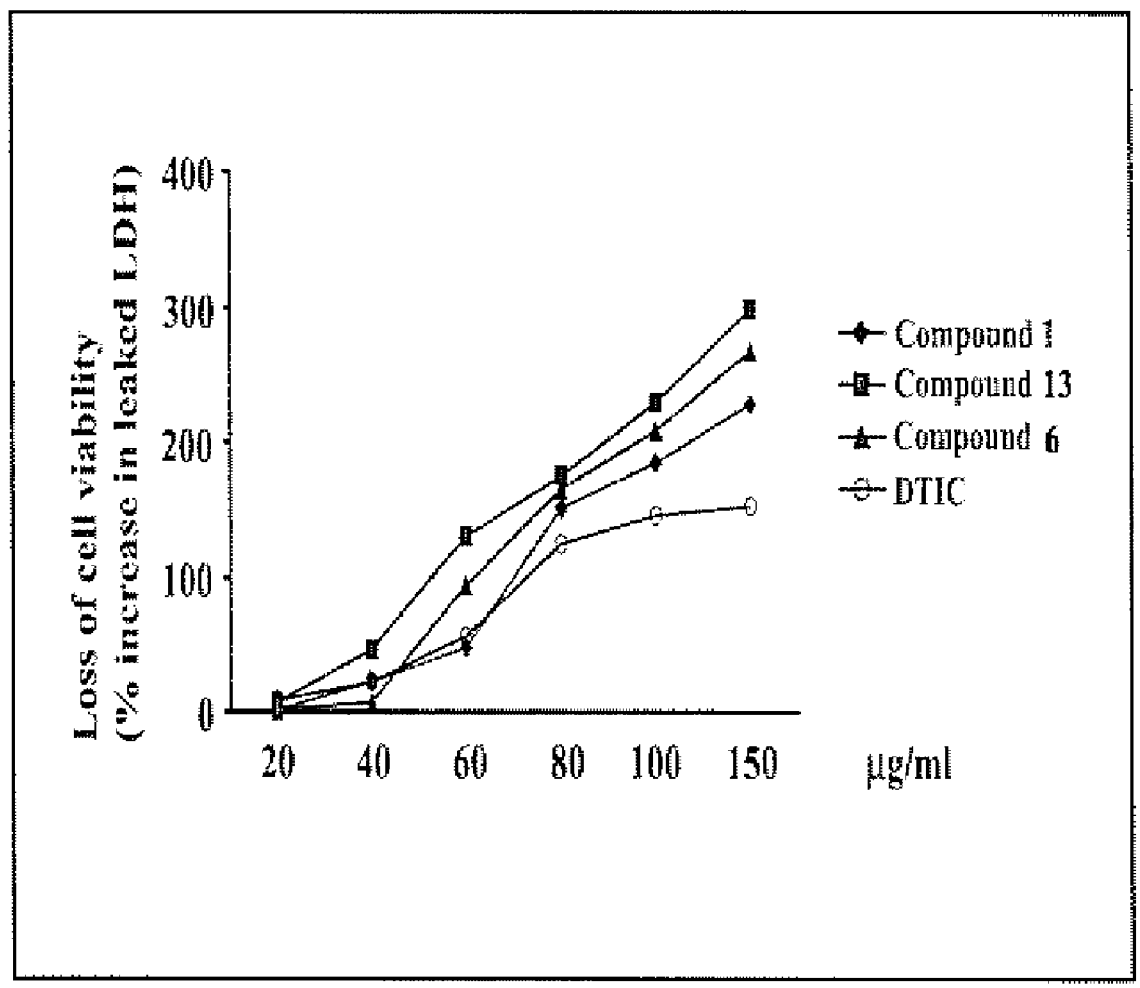
FIG. 1 illustrates line diagram showing percent increase in leaked Lactate dehydrogenase (LDH) from A2058 human melanoma cells, treated with various concentrations of Compound 1, Compound 6, Compound 13 and DTIC. Each point indicates percent increase in leaked LDH with respect to the vehicle control cultures, calculated from a mean of quadruplicate wells.

These and other embodiments of the present invention will become evident upon reference to the following detailed examples and attached drawings.

DETAILED DESCRIPTION OF THE INVENTION

Melanoma to date is considered a chemotherapy resistant and very hard to treat. Currently, dacarbazine and temozolamide have been extensively used chemotherapeutic agents for treating metastatic malignant melanoma. However, the success rate is low and the side effects are high.

The metastatic malignant melanoma is continued to be an incurable disease with median survival of approximately 8 months and the probability of surviving 5 years after the diagnosis is less than 5%. Response rates to combination regimens are reproducibly higher than with standard dacarbazine. However, in order to unequivocally make a difference in the management of metastatic malignant melanoma, it is necessary to demonstrate significant efficacy for the drug alone first to achieve higher percentage of complete remission (CR). Only then, any other combination dose regimens involving chemotherapeutic drugs, interleukins, interferons, and like biological response modifiers would make the malignant melanoma treatment more manageable and controlled.

Therefore, in order for the dose regimen to be effective, possibly high melanin binding moieties such as lipophillic thiophene system could offer a therapeutic treatment having all the three biochemical mechanisms of action superior to DTIC (Dacarbazine) with positive outcome leading to significantly increase in obtaining complete responses.

So the molecular structure we have chosen initially for our strategy involved a five membered heterocyclic thiophene ring system, which resembles and occupies similar shape and size to phenyl ring and is lipophilic in nature. In addition, thiophene ring structure has additional advantages internally built in that would aid in increasing the efficacy of the molecule by itself.

Thus, the present invention aims to fulfill this unmet medical need of selectively binding to the targeted melanoma cells and sparing the normal cells thereby increasing the target to non-target cell ratio and further providing other related advantages as described herein.

Accordingly, in an effort to increase the melanin binding, initially several compounds involving heterocyclic thiophene ring system as a backbone were considered. Due to the presence of large size sulfur atom, the five membered thiophene ring system would attain similar size and shape to a lipophillic six membered phenyl ring system in space. The substituted thiophene ring system, thus, in addition to it's aromatic nature would offer resonance delocalization of electrons in the ring which may contribute to increased efficacy. Hence, in a test mode of a few thiophene based triazene analogs were synthesized and evaluated with DTIC for their efficacy in vitro. Because of better in vitro efficacy than DTIC of the initially designed compounds, characterizations involving in vivo efficacy and mode of actions were further evaluated. The novel triazene analogs of the present invention, compositions containing the same, and the uses of the analogs and compositions in therapeutic applications is described herein below.

For the purpose of the present invention, the phrase/expression 'thiophene triazene analogs' 'melanin binding analogs' 'novel analogs' are used herein below interchangeably throughout the text referring to compounds of formula I and Formula II.

The compounds of formula (I) and (II) of the present invention, thiophene triazene analogs, having high affinity for melanin, thereby enhancing efficacy more efficiently. Furthermore, in a preferred embodiment, the novel analogs of the present invention may have been specifically designed to bind melanin more efficiently such target to non-target ratio can be enhanced thereby decreasing the toxicity.

In one embodiment, the melanin binding analogs may be represented by the following:

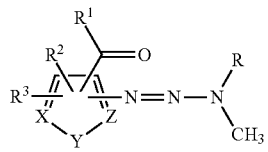

General formula I

Wherein,
R is independently selected from H, $CH_3$, $CH_2OH$
$R^1$ is independently selected from OH, $NHR^4$, $NR^4R^5$, SH
At least one of $R^2$, and $R^3$ is selected from H, N=N—N$(CH_3)_2$, N=N—$NHCH_3$, N=N—$N(CH_3)CH_2OH$, $CONHR^4$, $CONR^4R^5$, $CONHNH_2$, $CONHNHR^4$, $CONHNR^4R^5$, $COOCH_3$, $COOCH_2CH_3$, COOH, COSH, CN, C≡CH, $SO_2NH_2$, $SO_2NHR^4$, $SO_2NR^4R^5$, $SO_3H$, $SO_2CH_3$, $SO_2CH_2CH_2NH_2$, $NHCH_2COOH$, $NHCH(CH_3)$COOH, $NO_2$, $CF_3$, Cl, Br, F, I, $CCl_3$, Ph ($C_6H_5$), $CH_3$, $C_2H_5$, n-$C_3H_7$, iso-$C_3H_7$, n-$C_4H_9$, iso-$C_4H_9$, tert-$C_4H_9$, OH, $OCH_3$, $NH_2$, $NHCH_3$, etc. electron withdrawing and electron donating groups.
$R^4$ and $R^5$ are independently selected from H, $C_1$-$C_{10}$ alkyl, alkenyl, alkylol, alkylamine, etc.
X, Y, and Z are independently selected from C, N, O, and S such that the resulting five membered ring systems of the heterocyclic aromatic moieties are un-substituted and substituted thiophene, furan, thiazole, isothiazole, and furazole.

In another embodiment, the present invention also provides compounds of the formula (II):

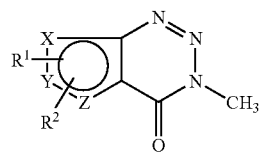

General formula II

Wherein,
At least one of $R^1$, and $R^2$ is independently selected from H, N=N—$N(CH_3)_2$ N=N—$NHCH_3$, N=N—$N(CH_3)$$CH_2OH$, $CONH_2$, $CONHR^4$, $CONR^4R^5$, $CONHNH_2$, $CONHNHR^4$, $CONHNR^4R^5$, $COOCH_3$, $COOCH_2CH_3$, COOH, COSH, CN, C≡CH, $SO_2NH_2$, $SO_2NHR^4$, $SO_2NR^4R^5$, $SO_3H$, $SO_2CH_3$, $SO_2CH_2CH_2NH_2$, $NHCH_2COOH$, $NHCH(CH_3)COOH$, $NO_2$, $CF_3$, Cl, Br, F, I, $CCl_3$, Ph ($C_6H_5$)$CH_3$, $C_2H_5$, n-$C_3H_7$, iso-$C_3H_7$, n-$C_4H_9$, iso-$C_4H_9$, tert-$C_4H_9$, OH, $OCH_3$, $NH_2$, $NHCH_3$, etc. electron withdrawing and electron donating groups.
$R^4$ and $R^5$ are independently selected from H, $CH_3$, $C_1$-$C_{10}$ alkyl, alkenyl, alkylol, alkylamine, etc.
X, Y, and Z are independently selected from C, N O, and S such that the heterocyclic aromatic five membered ring of the fused bicyclic systems are un-substituted and substituted thiophene, furan, thiazole, isothiazole, and furazole. The compound of general formula (II) is not 3-methylthiopheno [3,2-d]1,2,3-triazin-4-one (X=Y=C; Z=S; $R^1$=$R^2$=H).

It is to be understood that the invention covers all combinations of particular embodiments of the invention as described herein above, consistent with the definition of the compounds of formula (I) and formula (II).

Some of the preferred thiophene triazene analogs of formula (I) and formula (II) according to the present invention, but not limited to are:

3-[(Dimethylamino)diazenyl]thiophene-2-carboxamide (compd. No. 1)
3-[(Dimethylamino)diazenyl]-4-bromothiophene-2-carboxamide (compd. No. 2)
3-[(Dimethylamino)diazenyl]-5-nitrothiophene-2-carboxamide (compd. No. 3)
4-[(Dimethylamino)diazenyl]-3-methoxythiophene-2,5-dicarboxamide (compd. No. 4)
3-[(Dimethylamino)diazenyl]-5-phenylthiophene-2-carboxamide (compd. No. 5)
3-[(Dimethylamino)diazenyl]thiophene-2-carboxylic acid (compd. No. 6)
3-[(Dimethylamino)diazenyl]-5-nitrothiophene-2-carboxylic acid (compd. No. 7)
3-[(Dimethylamino)diazenyl]-5-phenylthiophene-2-carboxylic acid (compd. No. 8)
{3-[(Dimethylamino)diazenyl](2-thienyl)}-N-(2-hydroxyethyl)-carboxamide (compd. No. 9)
{3-[(Dimethylamino)diazenyl](2-thienyl)}-N-methylcarboxamide (compd. No. 10)
N-(2-Aminoethyl){3-[(dimethylamino)diazenyl](2-thienyl)}-carboxamide (compd. No. 11)
4-[Dimethylamino)diazenyl]thiophene-2-carboxamide (compd. No. 12)
4-[Dimethylamino)diazenyl]thiophene-3-carboxamide (compd. No. 13)
Potassium salt of 3-[(dimethylamino)diazenyl]thiophene-2-carboxylic acid (compd. No. 14)
3-Methylthiopheno[2,3-d]1,2,3-triazin-4-one (compd. No. 15)
3-Methyl-6-nitrothiopheno[2,3-d]1,2,3-triazin-4-one (compd. No. 16)
6-Amino-3-methylthiopheno[2,3-d]1,2,3-triazin-4-one (compd. No. 17)
3-Methyl-6-phenylthiopheno[3,2-d]1,2,3-triazin-4-one (compd. No. 18)

In the present invention, the compounds of the formulae (I) and (II) are disclosed together because of their structural similarities. For example, the inactive compound of formula (I) upon in vivo activation by liver microsomal enzymes (cytochrome P450) followed by oxidative demethylation, affords active monomethyltriazene analog. Likewise, the compound of formula (II) upon in vivo hydrolysis affords similar monomethyltriazene analog of the enzymatically active species that derived from formula (I). Therefore, due to the similarities of their metabolites in vivo, in one embodiment, compound of formula (I) was disclosed, and in an another embodiment, compound of formula (II) were disclosed. Thus, the compounds of formula (I) and formula (II) are disclosed due to convenience and should be considered structurally similar due to biological reasons.

Synthesis of Triazene Analogs

According to another feature of the present invention, there is provided a process as shown in the schemes, for the preparation of triazene analogs of the general formula (I) and formula (II), wherein all the groups are as defined earlier.

Compounds (1-8) of the general formula (I) can be produced according to the following method as shown in scheme A

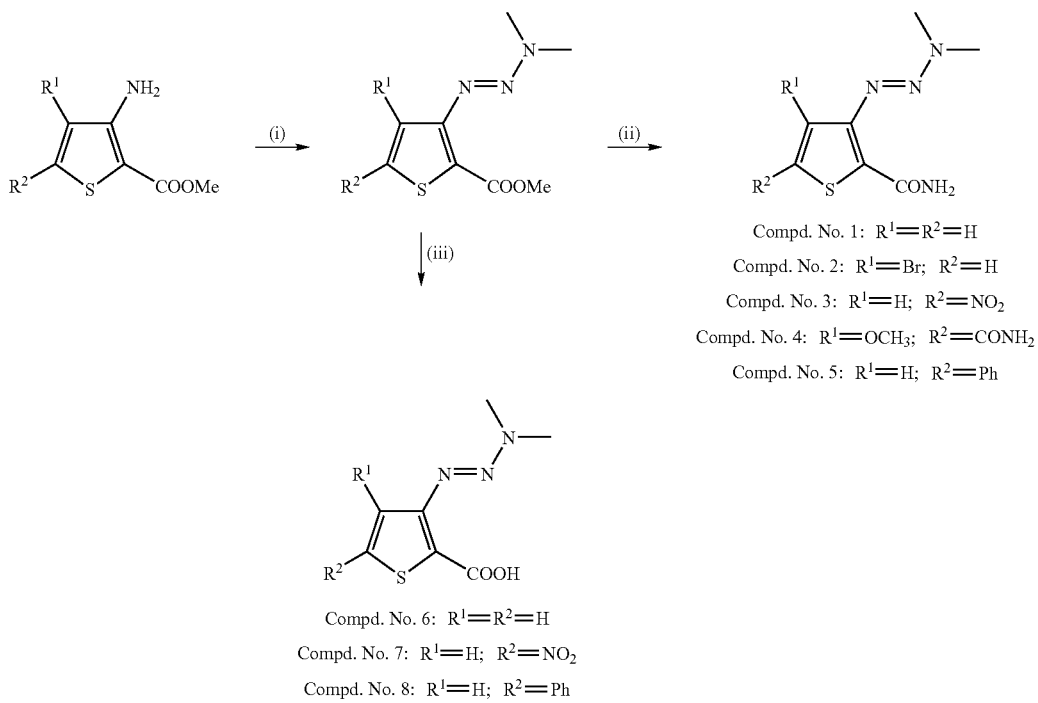

Diazotization of methyl 3-aminothiophene-2-carboxylate or its precursors with sodium nitrite followed by treatment with dimethylamine provides methyl 3-[(dimethylamino)diazenyl]thiophene-2-carboxylate or its derivatives in good yield. Treatment of the above esters with ammonia gave the triazene analogs of formula (I) (3-[(dimethylamino)diazenyl]thiophene-2-carboxamide (compd No. 1), compd. No. 2, compd. No. 3, compd. No. 4, compd. No. 5).

Hydrolysis of methyl 3-[(dimethylamino)diazenyl]thiophene-2-carboxylate or its derivatives with aqueous sodium hydroxide in methanol provided the triazene acid analogs of formula (I) (Compd. No. 6, compd. No. 7 and compd. No. 8).

The precursor compounds used in scheme A were produced in the following manner: Methyl 3-amino-4-bromothiophene-2-carboxylate is prepared by the bromination of methyl 3-aminothiophene-2-carboxylate (Aldrich).

Nitration of methyl 4-hydroxy-5-(methoxycarbonyl)thiophene-2-carboxylate (30) gave methyl 4-hydroxy-5-(methoxycarbonyl)-3-nitrothiophene-2-carboxylate, which was then methylated using dimethyl sulfate to produce methyl 4-methoxy-5-(methoxycarbonyl)-3-nitrothiophene-2-carboxylate. Reduction of nitro group with iron and HCl gave methyl 3-amino-4-methoxy-5-(methoxycarbonyl)thiophene-2-carboxylate. Methyl 3-amino-5-phenylthiophene-2-carboxylate is prepared by the known procedure (31, 32).

Compounds (9-11) of the general formula (I) can be produced according to the following method as shown in scheme B

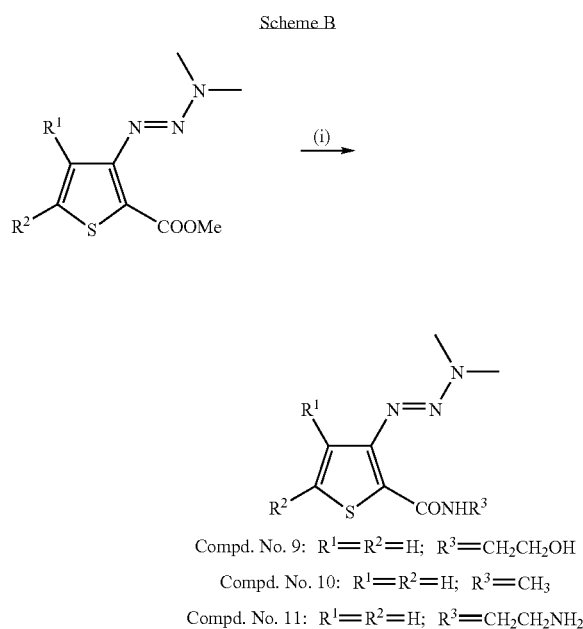

Compd. No. 9: $R^1=R^2=H$; $R^3=CH_2CH_2OH$
Compd. No. 10: $R^1=R^2=H$; $R^3=CH_3$
Compd. No. 11: $R^1=R^2=H$; $R^3=CH_2CH_2NH_2$ Reagents & conditions:
(i) $NH_2CH_2CH_2OH$ or $NH_2CH_3$ or $NH_2CH_2CH_2NH_2$, rt Treatment of methyl 3-[(dimethylamino)diazenyl]thiophene-2-carboxylate with various amines such as methyl amine, ethanol amine and ethylenediamine provides the corresponding triazene amide analogs of formula (I) (compd. No. 9, compd. No. 10, and compd. No. 11).

Compound (12) of the general formula (I) can be produced according to the following method as shown in scheme C

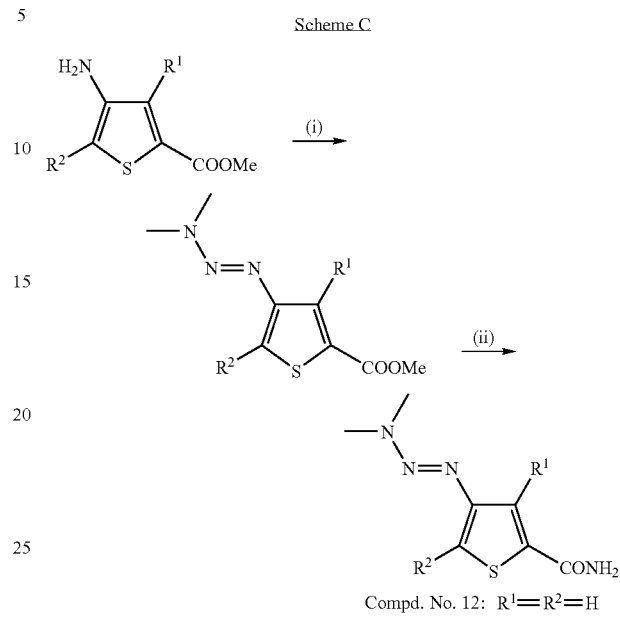

Compd. No. 12: $R^1=R^2=H$

Reagents & conditions:
(i) HCl, $NaNO_2$, dimethylamine, 0° C.
(ii) $NH_3$, rt

Diazotization of methyl 4-aminothiophene-2-carboxylate with sodium nitrite followed by treatment with dimethylamine provides methyl 4-[(dimethylamino)diazenyl]thiophene-2-carboxylate. Treatment of the ester with ammonia gave the required 4-[dimethylamino)diazenyl]thiophene-2-carboxamide (compd. No. 12). The precursor compound, methyl 4-aminothiophene-2-carboxylate is produced from the commercially available thiophene-2-carboxylic acid. The nitration of thiophene-2-carboxylic acid provides an inseparable mixture of 4-nitrothiophene-2-carboxylic acid and 5-nitrothiophene-2-carboxylic acid, which is esterified to get the corresponding esters. The nitro functionality is then reduced to amines using iron powder and the mixture separated by silica gel column chromatography to obtain methyl 4-aminothiophene-2-carboxylate.

Compound (13) of the general formula (I) can be produced according to the following method as shown in scheme D

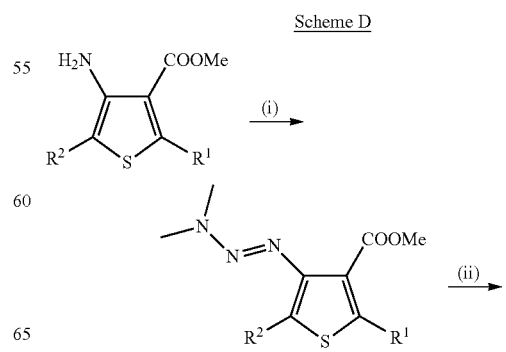

15
-continued

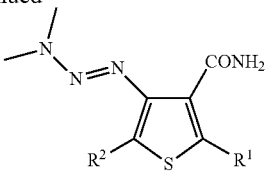

Compd. No. 13: $R^1 = R^2 = H$

Reagents & conditions:
(i) HCl, $NaNO_2$, dimethylamine, 0° C.
(ii) $NH_3$, rt

Diazotization of methyl 4-aminothiophene-3-carboxylate with sodium nitrite followed by treatment with dimethylamine provides methyl 4-[(dimethylamino)diazenyl]thiophene-3-carboxylate. Treatment of the ester with ammonia gave the required 4-[dimethylamino)diazenyl]thiophene-3-carboxamide (compd. No. 13). The methyl 4-aminothiophene-3-carboxylate is produced using known procedures in the prior art (33, 34, 35). Thus addition of methyl acrylate to methyl thioglycolate provided methyl 3-[(methoxycarbonyl)methylthio]propanoate in quantitative yield, which on cyclization in presence of sodium methoxide gave methyl 4-oxo-2,3,5-trihydrothiophene-3-carboxylate. Treatment of methyl 4-oxo-2,3,5-trihydrothiophene-3-carboxylate with hydroxylamine followed by basification with ammonia gave methyl 4-aminothiophene-3-carboxylate.

Compound (14) of the general formula (I) can be produced according to the following method as shown in scheme E Scheme E

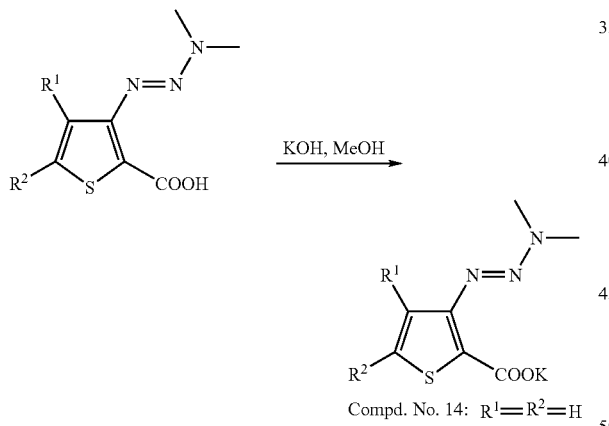

Compd. No. 14: $R^1 = R^2 = H$

Treatment of 3-[(dimethylamino)diazenyl]thiophene-2-carboxylic acid with potassium hydroxide in presence of methanol provided the corresponding potassium salt of triazene analog of formula (I), i.e., compd. No. 14.

Compounds (15-17) of the general formula (II) can be produced according to the following method as shown in scheme F Scheme F

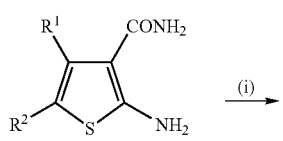

16
-continued

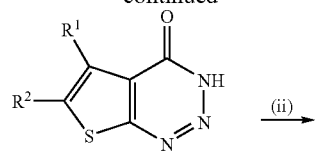

Compd. No. 15: $R^1 = R^2 = H$
Compd. No. 16: $R^1 = H$; $R^2 = NO_2$
Compd. No. 17: $R^1 = H$; $R^2 = NH_2$ Reagents & conditions:
(i) $H_2SO_4$, $NaNO_2$, 0° C.
(ii) $K_2CO_3$, $CH_3I$, acetone, rt Diazotization of 2-aminothiophene-3-carboxamide or its derivatives with sodium nitrite in presence of concentrated sulfuric acid produced 3H-thiopheno[2,3-d]1,2,3-triazin-4-one or its derivatives. Methylation of 3H-thiopheno[2,3-d]1,2,3-triazin-4-one or its derivatives with iodomethane in presence of potassium carbonate provided the corresponding triazene analogs of formula (II) (compd. No. 15, or compd. No. 16 or compd. No. 17). 2-Aminothiophene-3-carboxamide is produced from the known procedures in the prior art (36, 37) and the nitro derivative is prepared by the treatment of nitration mixture.

Compound (18) of the general formula (II) can be produced according to the following method as shown in scheme G Scheme G

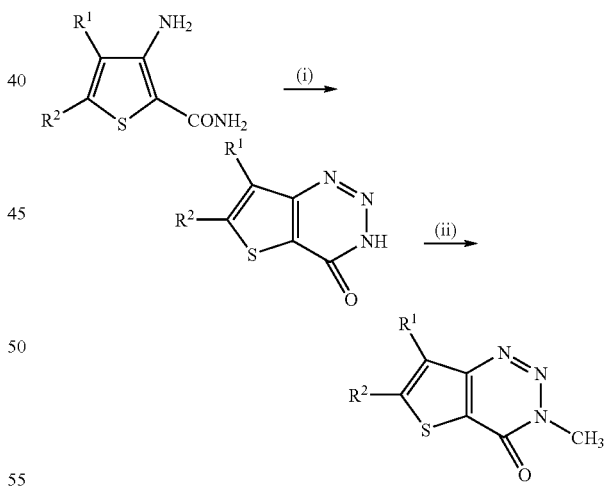

Compd. No. 18: $R^1 = H$; $R^2 = Ph$

Reagents & conditions:
(i) $H_2SO_4$, $NaNO_2$, 0° C.
(ii) $K_2CO_3$, $CH_3I$, acetone, rt Diazotization of 3-amino-5-phenylthiophene-2-carboxamide with sodium nitrite in presence of concentrated sulfuric acid produced 6-phenyl-3H-thiopheno[3,2-d]1,2,3-triazin-4-one. Methylation of 6-phenyl-3H-thiopheno[3,2-d]1,2,3-triazin-4-one with iodomethane in presence of potassium carbonate provided the corresponding triazene analog of formula (II), i.e., compd. No. 18.

In another embodiment, the method for the synthesis of triazene analogs of formula (I) comprises the diazotization of the corresponding amine compounds using metal nitrate and an acid; the resulting diazotized product may be reacted with amines in presence of a base; finally the triazene ester may be converted to a carboxylic acid or a carboxylic amide.

The method for the synthesis of triazene analogs of formula (I), wherein metal nitrate used in diazotization step is selected from sodium nitrite or potassium nitrite and acid is selected from inorganic acid or organic acid. The inorganic acid may be hydrochloric acid, sulfuric acid, and the like and the organic acid may be benzoic acid, para-toluenesulfonic acid and the like.

The method for the synthesis of triazene analogs of formula (I), wherein the diazotized product may be reacted with amine and the amine is selected from primary amine such as methyl amine, ethyl amine etc., or secondary amine such as dimethyl amine, diethyl amine etc.

The method for the synthesis of triazene analogs of formula (I), wherein the analog of carboxylic acid may be produced by the hydrolysis of the corresponding ester using metal hydroxide in presence of a solvent. The metal hydroxide may be selected from sodium hydroxide or potassium hydroxide etc., and the solvent is selected from water, methanol, ethanol, or mixtures thereof.

The method for the synthesis of triazene analogs of formula (I), where the analog of carboxamide may be produced by the treatment of the corresponding ester with amine in presence of a base in a solvent at ambient temperature. The amine may be selected from ammonia, methyl amine, ethanol amine, ethylene diamine etc., and the base is selected from potassium carbonate, sodium carbonate, sodium hydroxide, potassium hydroxide, pyridine, triethyl amine etc., and the solvent is selected from tetrahydrofuran, methanol, ethanol, acetone, water or mixtures thereof.

In another embodiment, the present invention encompasses pharmaceutically acceptable salts of the compounds of the formula (I), and formula (II), for example organic or inorganic acid addition salts. The triazene analogs of the above formula (I) and formula (II) and derivatives thereof, may be in the form of a solvate or a pharmaceutically acceptable salt, e.g., an acid addition or base addition salt. Such salts include hydrochloride, sulfate, phosphate, citrate, fumarate, methanesulfonate, acetate, tartrate, maleate, lactate, mandelate, succinate, oxalate, amino acids, and other suitable salts known in the art.

In another embodiment, the invention encompasses the optical enantiomers or diastereomers of the optically active compounds of formula (I), and formula (II).

Compositions Containing Triazene Analogs

The present invention provides a pharmaceutical or veterinary composition (hereinafter, simply referred to as a pharmaceutical composition) that may contain a melanin targeted analog as described above, in admixture with a pharmaceutically acceptable carrier or diluents. The invention provides a pharmaceutical composition that may contain a melanin targeted analog as described above, in admixture with a pharmaceutically acceptable carrier or diluent.

The pharmaceutical compositions of the present invention may be in any form which allows for the composition to be administered to a subject. For example, the composition may be in the form of a solid, liquid or gas (aerosol). Typical routes of administration include, without limitation, oral, topical, parenteral, sublingual, and rectal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a subject. Compositions that will be administered to a subject take the form of one or more dosage units, where for example, a tablet may be a single dosage unit, and a container of triazene in topical form may hold a plurality of dosage units.

Materials used in preparing the pharmaceutical compositions should be pharmaceutically pure and non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the particular form of the active ingredient, the manner of administration and the composition employed.

In general, the pharmaceutical composition may include a melanin targeted analog or derivative thereof as described herein, in admixture with one or more carriers. The carrier(s) may be particulate, so that the compositions are, for example, in tablet or powder form. The carrier(s) may be liquid, with the compositions being, for example oral syrup or injectable liquid. In addition, the carrier(s) may be gaseous, so as to provide an aerosol composition useful in e.g., inhalatory administration.

When intended for oral administration, the composition is preferably in either solid or liquid form, where semi-solid, semi-liquid, suspension and gel forms are included within the forms considered herein as either solid or liquid.

As a solid composition for oral administration, the composition may be formulated into a powder, granule, compressed tablet, pill, capsule, chewing gum, water or the like form. Such a solid composition will typically contain one or more inert diluents or edible carriers. In addition, one or more of the following adjuvants may be present: binders such as carboxymethylcellulose, ethyl cellulose, microcrystalline cellulose, or gelatin; excipients such as starch, lactose or dextrins, cyclodextrins, disintegrating agents such as alginic acid, sodium alginate, primogel, corn starch and the like; lubricants such as magnesium stearate or sterotex; glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it may contain, in addition to materials of the above type, a liquid carrier such as polyethylene glycol or a fatty oil.

The composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical composition of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid composition intended for either parenteral or oral administration should contain an amount of the triazene analog of formula (I) and/or formula (II) such that a suitable dosage will be obtained. Typically, this amount is at least 0.1% of a compound of the invention in the composition. When intended for oral administration, this amount may be varied to be between 0.1 and 80% of the weight of the composition. Preferred oral compositions contain between 4% and about 50% of the active triazene compound. Preferred compositions and preparations according to the present invention are prepared so that a parenteral dosage unit contains at least 0.01% to 1% by weight of triazene analogs of formula (I) and/or formula (II).

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or ionophoresis device. Topical formulations may contain at least 0.1 to about 10% w/v (weight per unit volume) concentration of the triazene analogs of formula (I) and/or formula (II).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol.

The composition may include various materials which modify the physical form of a solid or liquid dosage unit. For example, the composition may include materials that form a coating shell around the triazene analogs of formula (I) and/or formula (II). The materials which form the coating shell are typically inert, and may be selected from, for example sugar, shellac, and other enteric coating agents. Alternatively, the triazene analogs of formula (I) and/or formula (II) may be encased in a gelatin capsule.

The pharmaceutical composition of the present invention may consist of gaseous dosage units, e.g., it may be in the form of an aerosol. The term aerosol is used to denote a variety of systems ranging from those of colloidal nature to systems consisting of pressurized packages. Delivery may be by a liquefied or compressed gas or by a suitable pump system which dispenses the triazene analogs of formula (I) and/or formula (II). Aerosols of compounds of the invention may be delivered in monophasic, biphasic, or triphasic systems in order to deliver the triazene analogs of formula (I) and/or formula (II). Delivery of the aerosol includes the necessary container, activators, valves, sub-containers, spacers and the like, which together may form a kit. Preferred aerosols may be determined by one skilled in the art, without undue experimentation.

In another embodiment, a pharmaceutical composition of the present invention comprising a compound of formula (I) and/or formula (II) or pharmaceutically acceptable salt thereof, and at least one chemotherapeutic agent and optionally a pharmaceutically acceptable diluent or carrier.

The composition as said above, wherein said chemotherapeutic agent is selected from the group consisting of dacarbazine (DTIC), temozolamide, methotrexate, doxorubicin, cytoxan, 5-fluorouracil, cis-platin, carboplatin, oxaliplatin, vincristine, vinblastine, etoposide, irinotecan, topotecan, paclitaxel, docetaxel, taxotere, taxol, tamoxifen, gefitinib, adriamycin, gemcitabine, melphalan, streptozocin, floxuridine, 6-mercaptopurine, bleomycin, daunorubicin, Mitomycin-C, amsacrine, procabazine, capecitabine, avastin, herceptin, bexxar, velcade, zevalin, xeloda, erbitux (cetuximab), rituximab, campath (Alemtuzumab) and the like.

A composition intended to be administered by injection can be prepared by combining the triazene analogs of formula (I) and/or formula (II) with water so as to form a solution. A surfactant may be added to facilitate the formation of a homogeneous solution or suspension. Surfactants are compounds that non-covalently interact with the triazene analog or derivative so as to facilitate dissolution or homogeneous suspension of the triazene analogs of formula (I) and/or formula (II).

An effective amount of a compound or composition of the present invention is used to treat diseases of cells having melanoma and other cancers. These cells are typically mammalian cells. Methods of administering effective amounts of the triazene analogs of formula (I) and/or formula (II) are well known in the art and include the administration of inhalation, oral or parenteral forms. Such dosage forms include, but are not limited to, parenteral solutions, tablets, capsules, sustained release implants and transdermal delivery systems; or inhalation dosage systems employing dry powder inhalers or pressurized multi-dose inhalation devices. The dosage amount and frequency are selected to create an effective level of the agent without harmful effects. It will generally have a dosage range of about 0.01 to 100 mg/kg/day for efficacy, and typically about 2 to 10 mg/kg/day where administered orally or intravenously and about 0.1 to 4 mg/kg/day where administered intranasally or by inhalation.

A pharmaceutical composition comprising at least one compound of formula (I) and/or formula (II) or pharmaceutically acceptable salt thereof, and at least one chemotherapeutic agent and at lest one biologic response modifying agent and optionally a pharmaceutically acceptable diluent or carrier.

The composition containing at least one biologic response modifying agent as said above, wherein said biologic response modifying agent is selected from the group consisting of monoclonal antibodies, interferons (interferon-γ), interleukins (IL-1, IL-2, IL-9, IL-11, IL-12), various types of colony stimulating factors (CSF, GM-CSF, G-CSF), TNF-α receptor blocker drugs (TNF-α), and the like.

Kits Containing Triazene Analogs, and Preparation and Uses Thereof

In another embodiment of the invention, a triazene analog as described above may be included in a kit for producing a triazene analog of the invention (melanin targeted analog) for pharmaceutical use. Such kits generally will be used in hospitals, clinics or other medical facilities with ready access on a daily basis to formulate such formulations.

A method for inhibiting cancer cell growth or killing cancer cell in a patient by administering to said patient a therapeutically effective amount of compounds of formula (I) and formula (II).

A method of treating a subject suffering from cancer disease, wherein said cancer disease is of any type (solid, liquid, and lymphatic origin), and not limited to metastatic malignant melanoma, lymphomas (Hodgkins and non-Hodgkins), sarcomas (Ewing's sarcoma), carcinomas, brain tumors, central nervous system (CNS) metastases, gliomas, breast cancer, prostate cancer, lung cancer (small cell and non-small cell), colon cancer, pancreatic cancer, Head and Neck cancers, oropharyngeal squamous cell carcinoma, comprising the step of administering to said subject, an effective amount of compounds of formula (I) and/or formula (II).

A method for inhibiting cancer cell growth or killing cancer cell in a patient as said above, wherein a cancer cell is originated from any part of the body, and not limited to any organ of human body such as brain, lung, adrenal glands, pituitary gland, breast, prostate, pancreas, ovaries, Gastro Intestinal Tract, kidneys, Liver, spleen, testicles, cervix, upper, lower, or middle esophagus either primary or secondary tumors of all types.

A method of administration of compounds of formula (I) and formula (II) to a patient by any mode of delivery, but not limited to intraperitoneal (IP), intravenous (IV), oral (PO), intramuscular (IM), intracutaneous (IC), intradermal (ID), intrauterine, intrarectal and the like.

A method of administration of compounds of formula (I) and/or formula (II) using nanoparticles of different sizes in an emulsion to a patient, in need thereof.

Anti-Tumor Activity

We assessed the anti-tumor potential of triazene analogs of formula (I) and formula (II). The cell proliferation assay based on MTT incorporation in A2058 cell showed that the triazene analogs of formula (I) and formula (II) exhibit better efficacy in inhibition of tumor cell proliferation when compared to DTIC (Table 1). The 50% inhibitory concentration ($IC_{50}$) of some of the triazene analogs of the formula (I) and formula (II) were found to exhibit better activity when compare to that shown by standard drug (DTIC).

Figure 7:
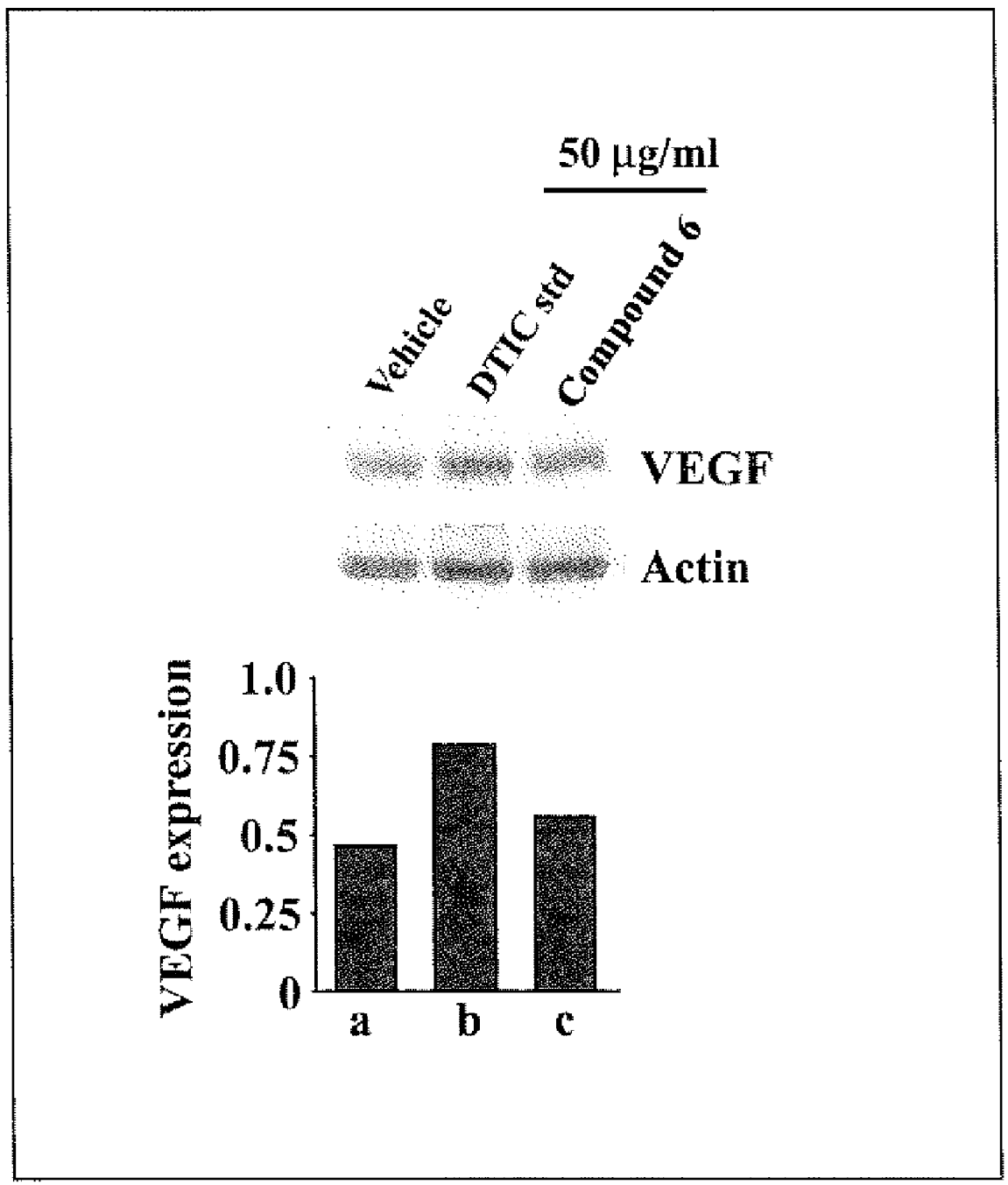
FIG. 7 represents immunoblot image showing down-regulation of VEGF protein in Compound 6 treated B16F0 cells. Bar diagram represents the normalized expression of VEGF protein in arbitrary units. Each bar represents the average expression calculated from at least three independent experiments.
Figure 9:
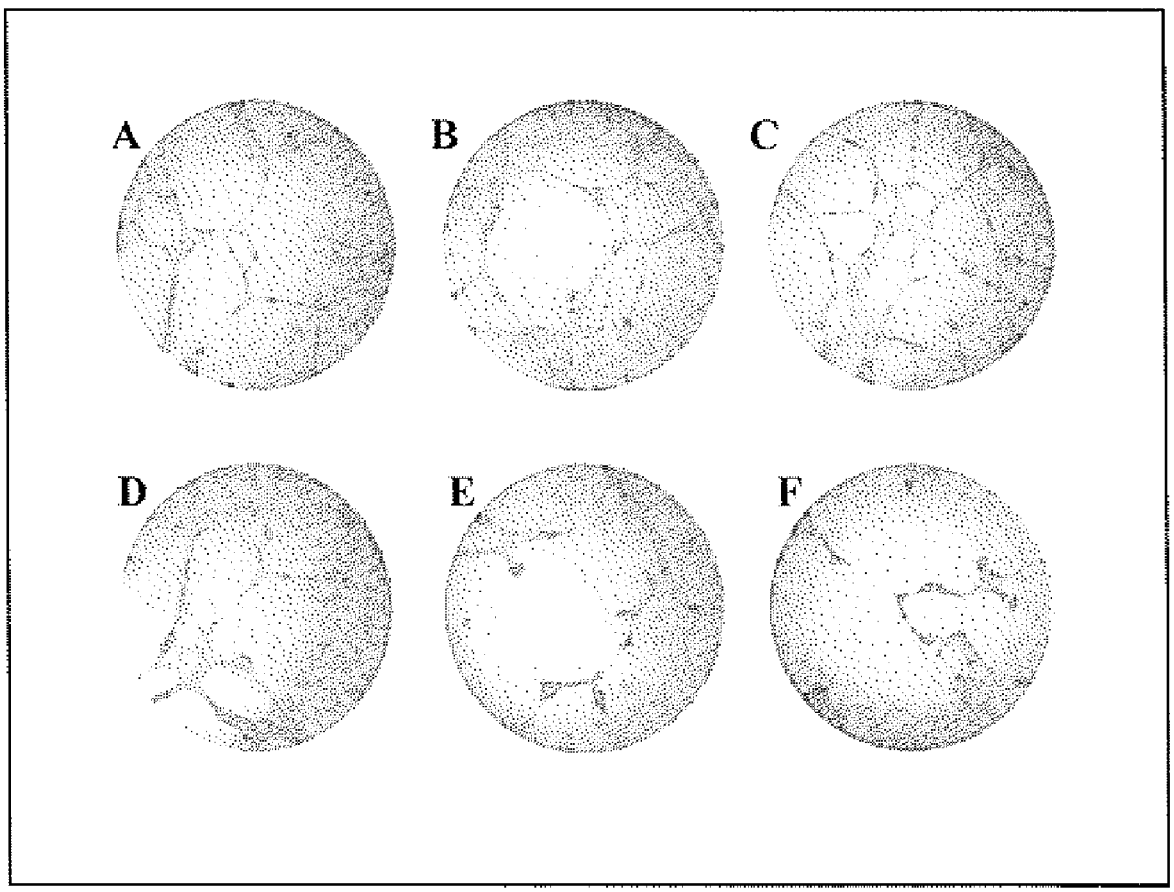
FIG. 9 shows inhibition of capillary-like tube formation by Compound 6. Human umbilical vein endothelial cells (HUVECs) were laid on Cultrex coated plates in presence of either DTIC (25 and 50 µg/ml at panels B and C, respectively) or Compound 6 (25 and 50 µg/ml at panels E and F, respectively) and allowed to form endothelial capillary tubes for 16 h at 37° C. Panels A and D represent capillary-like tube formation in 0.1% DMSO treated vehicle control wells.
Figure 10:
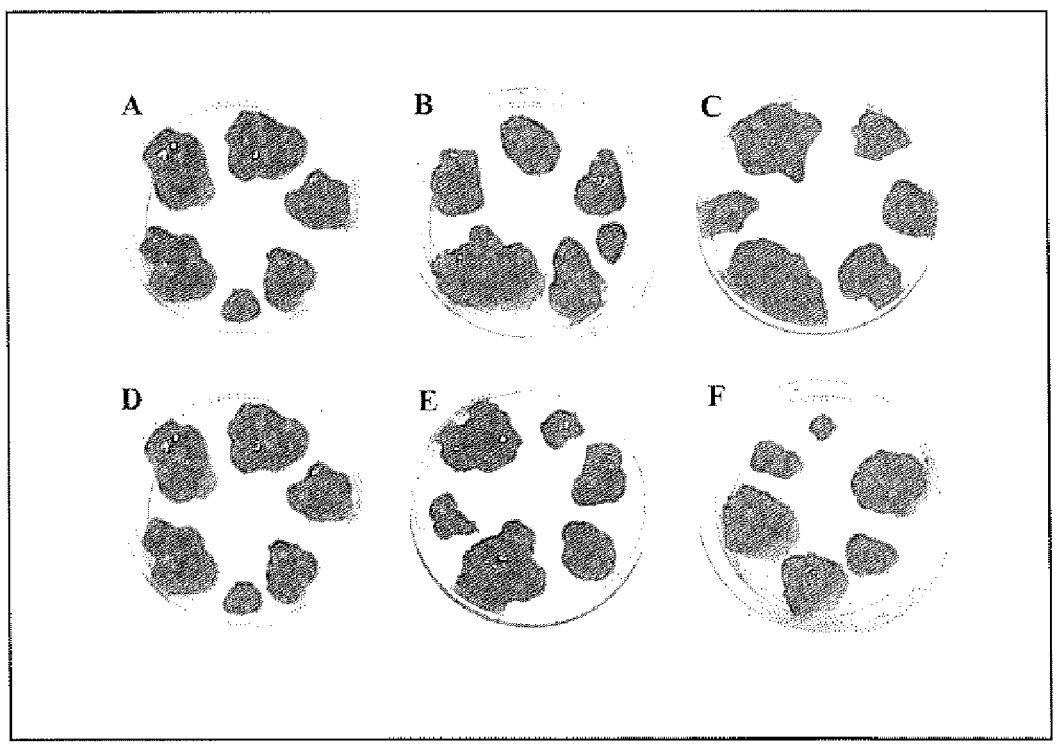
FIG. 10 shows efficacy of Compound 6 and DTIC against B16F0 tumor growth in C57B61 mice in vivo. The upper panel shows the photographs representing the size of tumors excised from sacrificed animals included in vehicle control (A and D), groups treated with 50 and 100 mg/kg of DTIC (B and C) and groups treated with 50 and 100 mg/kg of Compound 6 (E and F), respectively. Lower panel, table represents the average tumor weight in the respective groups (n=6) as indicated. Percent inhibition of tumor growth achieved in each group was calculated in comparison with the vehicle control group.

Similarly, the compound 6 of formula (I) showed better anti-tumor activity than DTIC in B16 F0 melanoma xenograft model of C57B6J mice. In addition, compound 6 also showed dose response inhibition at the two dose levels tested. However, DTIC failed to show statistically significant dose response at the same two dose levels tested (FIG. 10). The failure of DTIC to demonstrate dose response is consistent with the literature reports, indicating that DTIC is an angiogenesis promoter, while our finding indicated that compound 6 is an angiogenesis inhibitor (FIGS. 7, 9).

The present invention is provided by the examples given below, which are provided by the way of illustration only, and should not be considered to limit the scope of the invention. Variation and changes, which are obvious to one skilled in the art, are intended to be within the scope and nature of the invention, which are defined in the appended claims.

EXAMPLES

Example 1

Synthesis of 3-[(dimethylamino)diazenyl]thiophene-2-carboxamide (Compound 1)

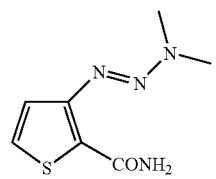

Step a:

Methyl 3-[(dimethylamino)diazenyl]thiophene-2-carboxylate: To a solution of methyl 3-aminothiophene-2-carboxylate (0.5 g, 3.18 mmol) and conc. HCl (1.3 mL, 12.73 mmol) in $H_2O$ (7.5 mL) was added $NaNO_2$ (0.24 g, 3.50 mmol) in portions for 5 min at 0° C. After stirring for 0.5 h at 0-5° C., the reaction mixture was added to the solution of $K_2CO_3$ (1.66 g, 12.09 mmol) and dimethylamine (1.3 mL, 40%, 11.46 mmol) in $H_2O$ (9 mL) at 0° C. The mixture was stirred at 0-5° C. for 1 h and poured into ice cold water. The solution was extracted with chloroform (3×30 mL). The combined $CHCl_3$ layer was washed with water, brine and dried over sodium sulfate. The solution was filtered and evaporated the solvent. The residue was chromatographed over silica gel column using hexane-EtOAc (80:20) as eluents to give the product as pale orange color solid (600 mg, 88%), mp 74-76° C. $^1$H NMR (400 MHz, $CDCl_3$): δ 7.33 (1H, d, J=5.6 Hz), 7.24 (1H, d, J=5.6 Hz), 3.87 (3H, s), 3.52 (3H, s), 3.29 (3H, s); LC-MS (positive ion mode): m/z 214 (M+H)$^+$.

Step b:

3-[(Dimethylamino)diazenyl]thiophene-2-carboxamide: To an ice cold (0-5° C.) solution of ammonium hydroxide (20 mL) was added a solution of methyl 3-[(dimethylamino)diazenyl]thiophene-2-carboxylate (600 mg) in THF (5 mL) for 5 min and stirred at rt for 20 h. The solution was poured into ice cooled water and the precipitated solid was filtered and dried to give crude product, which was chromatographed over silica gel column using chloroform-methanol (98:2) as eluents to give the product as an off-white solid (400 mg, 72%), mp 168-170° C. IR (neat) $v_{max}$ 3337, 3172, 2923, 1636, 1599, 1348, 1219, 1117, 884, 771 cm$^{-1}$; $^1$H NMR (400 MHz, $CDCl_3$): δ 8.28 (2H, br s), 7.35 (1H, d, J=5.6 Hz), 7.31 (1H, d, J=5.6 Hz), 3.58 (3H, br s), 3.20 (3H, br s); LC-MS (positive ion mode): m/z 221 (M+Na)$^+$.

Example 2

Synthesis of 3-[(dimethylamino)diazenyl]-4-bromothiophene-2-carboxamide (Compound 2)

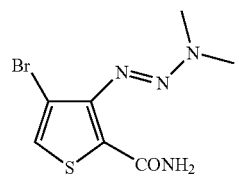

Step a:

Methyl 3-amino-4-bromothiophene-2-carboxylate: To a solution of methyl 3-aminothiophene-2-carboxylate (1 g, 6.36 mmol) in acetic acid (10 mL) was added a solution of bromine (0.32 mL, 6.36 mmol) in acetic acid (1 mL) slowly for 5 min at rt and stirred at the same temperature for 16 h. The reaction mixture was poured into ice cold water and extracted with chloroform (3×100 mL). The combined organic layer was washed with water, brine and dried over sodium sulfate. The solution was filtered and evaporated the solvent. The residue was chromatographed over silica gel column using hexane-EtOAc (95:5) as eluents to give the product as a pale yellow color solid (0.5 g, 33%), mp 58-60° C.

$^1$H NMR (400 MHz, $CDCl_3$): δ 7.29 (1H, s), 5.63 (2H, br s), 3.85 (3H, s).

Step b:

Methyl 3-[dimethylamino)diazenyl]-4-bromothiophene-2-carboxylate: To a solution of methyl 3-amino-4-bromothiophene-2-carboxylate (0.5 g, 2.11 mmol) and conc. HCl (0.85 mL, 8.47 mmol) in $H_2O$ (5 mL) was added $NaNO_2$ (160 mg, 2.33 mmol) in portions for 5 min at 0° C. After stirring 0.5 h at (0-5° C.), the reaction mixture was added to the solution of K$_2$CO$_3$ (1.1 g, 8.04 mmol) and dimethylamine (0.85 mL, 40%, 7.6 mmol) in H$_2$O (6 mL) at 0° C. The mixture was stirred at 0-10° C. for 1 h and poured into ice cold water. The solution was extracted with chloroform (3×30 mL). The combined CHCl$_3$ layer was washed with water, brine and dried over sodium sulfate. The solution was filtered and evaporated the solvent. The residue was chromatographed over silica gel column using hexane-EtOAc (90:10) as eluents to give the product as a pale orange color oil (0.5 g, 81%). $^1$H NMR (400 MHz, CDCl$_3$): δ 7.38 (1H, s), 3.80 (3H, s), 3.53 (3H, br s), 3.28 (3H, br s).

Step c:

3-[(Dimethylamino)diazenyl]-4-bromothiophene-2-carboxamide: To an ice cold (0-5° C.) solution of ammonium hydroxide (10 mL) was added a solution of methyl 3-[(dimethylamino)diazenyl]-4-bromothiophene-2-carboxylate (500 mg) in THF (5 mL) for 5 min and stirred at rt for 20 h. The solution was poured into ice cooled water and extracted with ethyl acetate (3×50 mL). The combined EtOAc layer was washed with water, brine and dried over sodium sulfate. The solution was filtered and evaporated the solvent. The residue was chromatographed over silica gel column using chloroform-methanol (98:2) as eluents to give the product as an off-white solid (250 mg, 53%), mp 194-196° C. $^1$H NMR (400 MHz, DMSO-d$_6$): δ 7.85 (1H, s), 7.75 (1H, br s), 7.56 (1H, br s), 3.56 (3H, br s), 3.21 (3H, br s); LC-MS (positive ion mode): m/z 277, 279 (M+H)$^+$.

Example 3

Synthesis of 3-[(dimethylamino)diazenyl]-5-nitrothiophene-2-carboxamide (Compound 3)

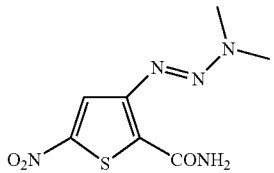

Step a:

Methyl 3-[(dimethylamino)diazenyl]thiophene-2-carboxylate: To a solution of methyl 3-aminothiophene-2-carboxylate (2.0 g, 12.7 mmol) and conc. HCl (5 mL, 50.8 mmol) in H$_2$O (30 mL) was added NaNO$_2$ (0.96 g, 14.08 mmol) in portions for 5 min at 0° C. After stirring 0.5 h (0-5° C.), the reaction mixture was added to the solution of K$_2$CO$_3$ (6.65 g, 48.26 mmol) and dimethylamine (5.14 mL, 40%, 45.7 mmol) in H$_2$O (36 mL) at 0° C. The mixture was stirred at 0-10° C. for 1 h and poured into ice cold water. The solution was extracted with chloroform (3×100 mL). The combined layer was washed with water, brine and dried over sodium sulfate. The solution was filtered and evaporated the solvent. The residue was chromatographed over silica gel column using hexane-EtOAc (80:20) as eluents to give the product as a pale orange color solid (2.5 mg, 91%), mp 74-76° C.

Step b:

Methyl 3-[(dimethylamino)diazenyl]-5-nitrothiophene-2-carboxylate: Methyl 3-[(dimethylamino)diazenyl]thiophene-2-carboxylate (2 g, 9.38 mmol) was added slowly for 15 min at 0 to −5° C. to concentrated sulfuric acid (20 mL). Then concentrated nitric acid (0.54 mL, 70%, 10.7 mmol) was added to the above reaction mixture for 10 min and stirred at the same temperature for 1 h and rt for 16 h. The mixture was poured into ice cooled water and basified with ammonium hydroxide. The solution was extracted with chloroform (3×100 mL) and the combined organic layer was washed with water, brine and dried over sodium sulfate. The solution was filtered and evaporated the solvent. The residue was chromatographed over silica gel column using hexane-ethyl acetate (80:20) as eluents to give the product as a yellow color solid (450 mg, 26%), mp 128-130° C.

Step c:

3-[(Dimethylamino)diazenyl]-5-nitrothiophene-2-carboxamide: To an ice cold (0-5° C.) solution of ammonium hydroxide (35 mL) was added a solution of methyl 3-[(dimethylamino)diazenyl]-5-nitrothiophene-2-carboxylate (400 mg) in THF (10 mL) for 5 min and stirred at rt for 20 h. The solution was poured into ice cooled water and extracted with ethyl acetate (3×100 mL). The combined organic layer was washed with water, brine and dried over sodium sulfate. The solution was filtered and evaporated the solvent. The residue was chromatographed over silica gel column using hexane-ethyl acetate (50:50) as eluents to give the product as a yellow color solid (90 mg, 26%), mp 240-246° C. $^1$H NMR (400 MHz, DMSO-d$_6$): δ 8.22 (1H, s), 8.05 (1H, s), 7.91 (1H, s), 3.63 (3H, s), 3.26 (3H, s); LC-MS (positive ion mode): m/z 266 (M+Na)$^+$.

Example 4

Synthesis of 4-[(dimethylamino)diazenyl]-3-methoxythiophene-2,5-dicarboxamide (Compound 4)

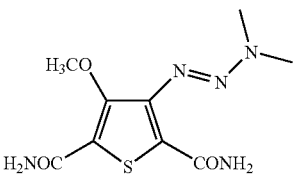

Step a:

Methyl 4-hydroxy-5-(methoxycarbonyl)-3-nitrothiophene-2-carboxylate: Methyl 4-hydroxy-5-(methoxycarbonyl)thiophene-2-carboxylate (5 g, 23.14 mmol) was added slowly for 15 min at 0 to −5° C. to concentrated sulfuric acid (25 mL). Then concentrated nitric acid (3.2 mL, 70%, 34.7 mmol) was added to the above reaction mixture for 10 min and stirred at the same temperature for 1 h. The mixture was poured into ice cooled water and extracted with ethyl acetate (3×100 mL). The combined organic layer was washed with water, brine and dried over sodium sulfate. The solution was filtered and evaporated the solvent. The residue was chromatographed over silica gel column using chloroform-methanol (95:5) as eluents to give the product as a yellow color semi-solid (1.2 g, 20%).

Step b:

Methyl 4-methoxy-5-(methoxycarbonyl)-3-nitrothiophene-2-carboxylate: To a solution of methyl 4-hydroxy-5-(methoxycarbonyl)-3-nitrothiophene-2-carboxylate (650 mg, 2.5 mmol) in acetone (20 mL) was added potassium carbonate (0.68 g, 5 mmol) at it Dimethyl sulfate (0.36 mL, 3.73 mmol) was added to the above reaction mixture slowly with stirring and a catalytic amount of KI was added. The mixture was refluxed for 4 h and the cooled reaction mixture was filtered and the solids were washed with acetone. Acetone was removed under reduced pressure and the residue was chromatographed over silica gel column using hexane-ethyl acetate (90:10) as eluents to give the product as a pale yellow color solid (0.3 g, 45%), mp 80-82° C. $^1$H NMR (400 MHz, CDCl$_3$): δ 4.08 (3H, s), 3.94 (3H, s), 3.92 (3H, s).

Step c:

Methyl 3-amino-4-methoxy-5-(methoxycarbonyl)thiophene-2-carboxylate: To a solution of methyl 4-methoxy-5-(methoxycarbonyl)-3-nitrothiophene-2-carboxylate (0.9 g, 3.27 mmol) in methanol (20 mL) was added conc. Hydrochloric acid (0.3 mL). To the above solution was added iron powder (0.91 g, 16.36 mmol) followed by an aqueous solution of ammonium chloride (0.87 g, 16.3 mmol, water: 5 mL) at rt. The reaction mixture was stirred and warmed to 70° C. for 1 h and was then allowed to cool to rt. The solution was filtered and basified with saturated sodium bicarbonate solution. The solution was extracted with ethyl acetate (4×100 mL). The combined organic layer was washed with brine and dried over sodium sulfate. The solution was filtered and evaporated the solvent to give the product as a pale yellow color solid (0.65 g, 81%), mp 120-124° C. NMR (400 MHz, CDCl$_3$): δ 5.39 (2H, br s), 4.01 (3H, s), 3.87 (3H, s), 3.85 (3H, s); LC-MS (positive ion mode): m/z 246 (M+H)$^+$.

Step d:

Methyl 3-[dimethylamino)diazenyl]-4-methoxy-5-(methoxycarbonyl)thiophene-2-carboxylate: To a solution of methyl 3-amino-4-methoxy-5-(methoxycarbonyl)thiophene-2-carboxylate (0.6 g, 2.44 mmol), conc. HCl (1 mL, 9.8 mmol) in H$_2$O (10 mL) and acetone (10 mL) was added NaNO$_2$ (0.19 g, 2.7 mmol) in portions for 5 min at 0° C. After stirring for 0.5 h at (0-5° C.), the reaction mixture was added to the solution of K$_2$CO$_3$ (1.28 g, 9.3 mmol) and dimethylamine (1 mL, 40%, 8.78 mmol) in H$_2$O (8 mL) at 0° C. The mixture was stirred at 0-10° C. for 1 h and poured into ice cold water. The solution was extracted with chloroform (3×100 mL). The combined CHCl$_3$ layer was washed with water, brine and dried over sodium sulfate. The solution was filtered and evaporated the solvent. The residue was chromatographed over silica gel column using hexane-EtOAc (80:20) as eluents to give the product as pale orange color oil (0.45 g, 62%). $^1$H NMR (400 MHz, CDCl$_3$): δ 3.93 (3H, s), 3.88 (3H, s), 3.82 (3H, s), 3.53 (3H, br s), 3.26 (31-1, br s); LC-MS (positive ion mode): m/z 324 (M+Na)$^+$.

Step e:

4-[(Dimethylamino)diazenyl]-3-methoxythiophene-2,5-dicarboxamide: To an ice cold (0-5° C.) solution of ammonium hydroxide (20 mL) was added a solution of methyl 3-[(dimethylamino)diazenyl]-4-methoxy-5-(methoxycarbonyl)thiophene-2-carboxylate (400 mg) in THF (5 mL) for 5 min and stirred at rt for 20 h. The solution was poured into ice cooled water and extracted with ethyl acetate (10×50 mL). The combined organic layer was washed with water, brine and dried over sodium sulfate. The solution was filtered and evaporated the solvent. The residue was crystallized from chloroform-methanol to give the product as an off-white color solid (80 mg, 22%), mp 226-228° C. $^1$H NMR (400 MHz, DMSO-d$_6$): δ 7.86 (1H, s), 7.81 (1H, s), 7.73 (1H, s), 7.35 (1H, s), 3.72 (3H, s), 3.59 (3H, br s), 3.21 (3H, br s); LC-MS (positive ion mode): m/z 294 (M+Na)$^+$.

Example 5

Synthesis of 3-[(dimethylamino)diazenyl]-5-phenylthiophene-2-carboxamide (Compound 5)

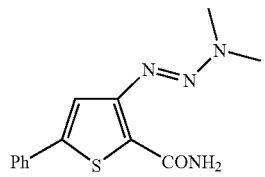

Step a:

3-Chloro-3-phenylprop-2-enenitrile: To an ice cold (0-5° C.) solution of dry dimethylformamide (25.6 mL, 333.2 mmol) was added phosphorous oxychloride (15.6 mL, 166.6 mmol) dropwise with stirring for 15 min. To this cold mixture, acetophenone (10 g, 83 mmol) was added dropwise maintaining the temperature of the reaction mixture between 45-55° C. for 10 min. The reaction mixture was slowly allowed to rt and stand for 30 min. To the reaction mixture, 7 mL of a total solution of hydroxylamine hydrochloride (23.1 g, 333.2 mmol) in dry DMF (33 mL) was added and the mixture was stirred at 70-80° C. for 5 min. Then the remaining solution of hydroxylamine hydrochloride in DMF was added thereafter at such a rate that the temperature of the reaction mixture rise above 145-155° C. After completion of the addition, the reaction mixture was allowed to rt for 30 min and diluted with cold water (0.5 L). The solution was extracted with chloroform and the chloroform layer was washed with water, brine and dried over sodium sulfate. The solution was filtered and evaporated the solvent. The residue was chromatographed over silica gel using hexane-ethyl acetate (98:2) as eluents to give the product as an oil (7 g, 52%). $^1$H NMR (400 MHz, CDCl$_3$): δ 7.64-7.67 (2H, m), 7.43-7.53 (3H, m), 6.02 (1H, s).

Step b:

Methyl 3-amino-5-phenylthiophene-2-carboxylate: To a solution of methyl thioglycolate (1 g, 9.43 mmol) in methanol (5 mL) was added a solution of sodium methoxide (0.5 g, 9.43 mmol) in methanol (5 mL) and stirred for 0.5 h. To the above mixture, a solution of 3-chloro-3-phenylprop-2-enenitrile (1.22 g, 7.5 mmol) in DMF (3.5 mL) was added dropwise for 10 min at rt and stirred the mixture at 60° C. for 2 h. Then, a solution of sodium methoxide (1 g, 18.6 mmol) in methanol (10 mL) was added dropwise at rt and stirring was continued for 2 h at 60° C. The mixture was allowed to rt and poured into cold water and stirred for 15 min. The solution was extracted with chloroform (3×100 mL) and the combined chloroform layer was washed with water, brine and dried over sodium sulfate. The solution was filtered and evaporated the solvent. The residue was chromatographed over silica gel using hexane-ethyl acetate (92:8) as eluent to give the product as a pale yellow color solid (1.1 g, 50%), mp 130-132° C. $^1$H NMR (400 MHz, DMSO-d$_6$): δ 7.62-7.65 (2H, m), 7.38-7.48 (3H, m), 7.00 (1H, s), 4.29 (2H, br s), 3.74 (3H, s); LC-MS (positive ion mode): m/z 234 (M+H)$^+$.

Step c:

Methyl 3-[(dimethylamino)diazenyl]-5-phenylthiophene-2-carboxylate: To a solution of methyl 3-amino-5-phenylthiophene-2-carboxylate (5 g, 21.4 mmol) and conc. HCl (9 mL, 85.8 mmol) in H$_2$O (51 mL) was added acetone (30 mL) to dissolve the product. Then NaNO$_2$ (1.7 g, 23.6 mmol) was added in portions for 15 min at 0° C. After stirring at 0-5° C. for 1 h, the reaction mixture was added to the solution of K$_2$CO$_3$ (11.2 g, 81.5 mmol) and dimethylamine (8.5 mL, 40%, 77.2 mmol) in H$_2$O (60 mL) at 0° C. The mixture was stirred at 0-5° C. for 1 h and poured into ice cold water. The solution was extracted with chloroform (3×100 mL). The combined CHCl$_3$ layer was washed with water, brine and dried over sodium sulfate. The solution was filtered and evaporated the solvent. The residue was chromatographed over silica gel column using hexane-EtOAc (90:10) as eluents to give the product as a pale brown color solid (3.8 g, 76%), mp 92-94° C. $^1$H NMR (400 MHz, DMSO-d$_6$): δ 7.78-7.80 (2H, m), 7.64 (1H, s), 7.46-7.52 (3H, m), 3.84 (3H, s), 3.60 (3H, s), 3.28 (3H, s); LC-MS (positive ion mode): m/z 290 (M+H)$^+$.

27

Step d:

3-[(Dimethylamino)diazenyl]-5-phenylthiophene-2-carboxamide: To an ice cold (0-5° C.) solution of ammonium hydroxide (80 mL) was added a solution of methyl 3-[(dimethylamino)diazenyl]-5-phenylthiophene-2-carboxylate (2.2 g) in THF (15 mL) for 5 min followed by catalytic amount of PEG-400 and the mixture was stirred at rt for 36 h. The solution was poured into ice cooled water and extracted with chloroform. The combined organic layer was washed with water, brine and dried over sodium sulfate. The solution was filtered and evaporated the solvent. The residue was chromatographed over silica gel column using chloroform-methanol (94:6) as eluents to give the product. The crude product was recrystallized from chloroform-hexane to give the product as a yellow color solid (170 mg, 8%), mp 220-222° C. IR (neat) $\nu_{max}$, 3343, 2922, 2855, 1642, 1595, 1221, 1023, 880, 841 cm$^{-1}$; $^1$H NMR (400 MHz, CDCl$_3$): δ 8.30 (1H, br s), 7.64-7.66 (2H, m), 7.53 (1H, s), 7.30-7.41 (3H, m), 6.34 (1H, br s), 3.59 (3H, s), 3.20 (3H, s); $^{13}$C NMR (100 MHz, CDCl$_3$): δ 164.7, 151.1, 146.7, 133.9, 128.9, 128.5, 125.8, 125.4, 114.7, 43.6, 36.5; LC-MS (positive ion mode): m/z 297 (M+Na)$^+$.

Example 6

Synthesis of 3-[(dimethylamino)diazenyl]thiophene-2-carboxylic acid (Compound 6)

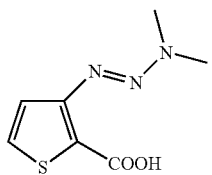

To a solution of methyl 3-[(dimethylamino)diazenyl]thiophene-2-carboxylate (200 mg, 0.93 mmol) in methanol (10 mL) was added a solution of sodium hydroxide (93 mg, 2.3 mmol) in water (2 mL) and stirred at rt for 2 h. The mixture was diluted with ice cold water and acidified with dil. HCl and extracted with chloroform. The combined chloroform layer was washed with water, brine and dried over sodium sulfate. The solution was filtered and evaporated the solvent. The residue was chromatographed over silica gel column using hexane-ethyl acetate (80:20) as eluents to give the product as an off-white solid (70 mg, 38%), mp 108-110° C. IR (neat) $\nu_{max}$ 3402, 3082, 2923, 1708, 1218, 1116, 1066, 1016, 880, 773 cm$^{-1}$; $^1$H NMR (400 MHz, CDCl$_3$): δ 12.21 (1H, s), 7.47 (1H, d, J=5.2 Hz), 7.30 (1H, d, J=5.2 Hz), 3.65 (3H, s), 3.28 (3H, s); LC-MS (positive ion mode): m/z 200 (M+H)$^+$.

Example 7

Synthesis of 3-[(dimethylamino)diazenyl]-5-nitrothiophene-2-carboxylic acid (Compound 7)

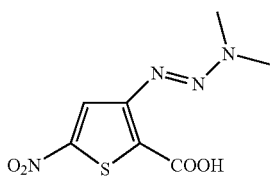

To a solution of methyl 3-[(dimethylamino)diazenyl]-5-nitrothiophene-2-carboxylate (550 mg) in methanol (10 mL) was added an aqueous solution of sodium hydroxide (0.25 g in 5 mL of water) at rt and stirred the mixture for 14 h. Excess of methanol was evaporated under reduced pressure and the residue was diluted with ice cold water. The solution was acidified with dil. HCl and the solid separated was filtered, washed with water and dried to give the product as a yellow color solid (450 mg, 86%). The crude product was recrystallized from chloroform-methanol (290 mg), mp 184-186° C. $^1$H NMR (400 MHz, DMSO-d$_6$): δ 13.26 (1H, br s), 8.00 (1H, s), 3.59 (3H, s), 3.25 (3H, s); LC-MS (positive ion mode): m/z 245 (M+H)$^+$.

Example 8

Synthesis of 3-[(dimethylamino)diazenyl]-5-phenylthiophene-2-carboxylic acid (Compound 8)

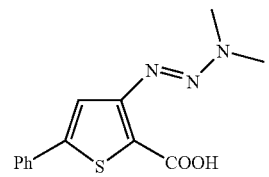

To a solution of methyl 3-[(dimethylamino)diazenyl]-5-phenylthiophene-2-carboxylate (1.8 g, 6.22 mmol) in methanol (50 mL) was added a solution of sodium hydroxide (1.24 g, 31.1 mmol) in water (15 mL) and stirred at rt for 16 h. The mixture was diluted with ice cold water and acidified with dil. HCl. The mixture was stirred for 30 min and the precipitated solid was filtered, washed with water and dried. The solid was chromatographed over silica gel column using hexane-ethyl acetate (70:30) as eluents to give the product. The crude solid was recrystallized from hexane-chloroform to give the product as a pale pink color solid (1.1 g, 61%), mp 162-166° C. IR (neat)$\nu_{max}$. 2923, 2853, 1708, 1260, 1220, 1173, 1042, 1020, 879, 836 cm$^{-1}$; $^1$H NMR (400 MHz, CDCl$_3$): δ 12.15 (1H, br s), 7.58-7.60 (2H, m), 7.44 (1H, s), 7.32-7.40 (3H, m), 3.65 (3H, s), 3.25 (3H, s); $^{13}$C NMR (100 MHz, CDCl$_3$): δ 162.8, 153.3, 149.7, 133.3, 129.1, 129.0, 125.9, 120.1, 113.4, 44.3, 37.0; LC-MS (positive ion mode): m/z 298 (M+Na)$^+$.

Example 9

Synthesis of {3-[(dimethylamino)diazenyl] (2-thienyl)}-N-(2-hydroxyethyl)-carboxamide (Compound 9)

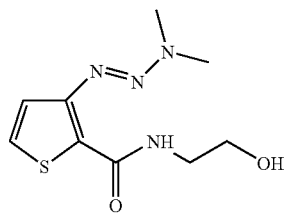

To an ice cold (0-5° C.) solution of ethanol amine (5 mL) in THF (5 mL) was added a solution of methyl 3-[(dimethylamino)diazenyl]thiophene-2-carboxylate (500 mg) in THF (5 mL) for 5 min and stirred at rt for 20 h. The solution was poured into ice cooled water and the solution was extracted with ethyl acetate (3×50 mL). The combined EtOAc layer was washed with water, brine and dried over sodium sulfate. The solution was filtered and evaporated the solvent. The residue was chromatographed over silica gel column using chloroform-methanol (95:5) as eluents to give the product, which was recrystallized from chloroform-hexane gave the product as a pale orange color solid (430 mg, 77%), mp 118-122° C. IR (neat) $v_{max}$, 3397, 3278, 2926, 1621, 1353, 1298, 1220, 1083, 1007, 882, 775 cm$^{-1}$;

$^1$H NMR (400 MHz, CDCl$_3$): δ 8.86 (1H, br s), 7.31 (1H, d, J=5.6 Hz), 7.28 (1H, d, J=5.2 Hz), 3.78-3.82 (2H, m), 3.60-3.64 (2H, m), 3.57 (3H, br s), 3.23 (3H, br s), 2.76 (1H, t, J=5.0 Hz); LC-MS (positive ion mode): m/z 243 (M+H)$^+$.

Example 10

Synthesis of {3-[(dimethylamino)diazenyl](2-thienyl)}-N-methylcarboxamide (Compound 10)

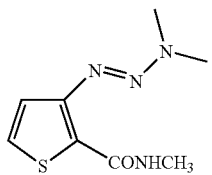

To an ice cold (0-5° C.) solution of methyl amine (3 mL) in THF (5 mL) was added a solution of methyl 3-[(dimethylamino)diazenyl]thiophene-2-carboxylate (500 mg) in THF (5 mL) for 5 min and stirred at rt for 36 h. The solution was poured into ice cooled water and the solution was extracted with chloroform (3×100 mL). The combined chloroform layer was washed with water, brine and dried over sodium sulfate. The solution was filtered and evaporated the solvent. The residue was chromatographed over silica gel column using chloroform-methanol (98:2) as eluents to give the product, which was recrystallized from chloroform-hexane gave the product as a pale orange color solid (380 mg, 76%), mp 98-102° C. IR (neat) $v_{max}$ 3297, 3082, 2929, 1637, 1380, 1348, 1299, 1221, 1109, 1016, 882, 776 cm$^{-1}$; $^1$H NMR (400 MHz, CDCl$_3$): δ 8.35 (1H, br s), 7.29 (1H, d, J=5.2 Hz), 7.27 (1H, d, J=5.2 Hz), 3.57 (3H, br s), 3.21 (3H, br s), 3.00 (3H, d, J=4.8 Hz); LC-MS (positive ion mode): m/z 213 (M+H)$^+$.

Example 11

Synthesis of N-(2-aminoethyl){3-[(dimethylamino)diazenyl](2-thienyl)}-carboxamide (Compound 11)

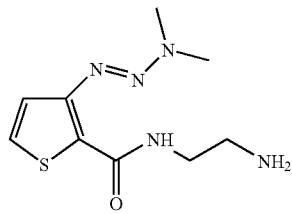

To an ice cold (0-5° C.) solution of ethylenediamine (5 mL) in ethanol (5 mL) was added a solution of methyl 3-[(dimethylamino)diazenyl]thiophene-2-carboxylate (250 mg) in ethanol (5 mL) for 5 min and stirred at rt for 24 h. The solution was poured into ice cooled water and saturated with sodium chloride. The solution was extracted with THF (3×100 mL). The combined THF layer was washed with brine and dried over sodium sulfate. The solution was filtered and evaporated the solvent. The residue was chromatographed over silica gel column using chloroform-methanol (90:10) as eluents to give the product as an off-white solid (60 mg, 22%), mp 98-100° C. $^1$H NMR (400 MHz, CDCl$_3$): δ 8.65 (1H, br s), 7.30 (1H, d, J=5.2 Hz), 7.28 (1H, d, J=5.2 Hz), 3.50-3.57 (5H, m). 3.24 (3H, br s), 2.91 (2H, t, J=6.0 Hz).

Example 12

Synthesis of 4-[dimethylamino)diazenyl]thiophene-2-carboxamide (Compound 12)

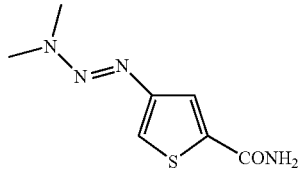

Step a:

4-Nitrothiophene-2-carboxylic acid: Sulfuric acid (3.0 mL, 5.505 g, 56.17 mmol) was added to nitric acid (2.0 mL, 2.98 g, 49.6 mmol) slowly at 0-10° C. After completion of the addition, thiophene-2-carboxylic acid (2.8 g, 21.87 mmol) was added to the above nitration mixture slowly for 15 min at the same temperature and stirred the mixture for 1 h. The reaction mixture was poured into ice cold water and stirred for 30 min. The precipitated solid was filtered, washed with cold water and dried. The filtrate was extracted with ethyl acetate. The combined ethyl acetate layer was washed with water, brine and dried over sodium sulfate. The solution was filtered and evaporated the solvent. The combined product was stirred with hexane (2×50 mL) and filtered the solid and dried to give the product as an off-white solid (2.8 g, 75%), mp 110-118° C. The product was a mixture of two compounds by HPLC and $^1$H NMR and was proceeded to the next step.

Step b:

Methyl 4-nitrothiophene-2-carboxylate: To a solution of nitrothiophene-2-carboxylic acids (6.8 g, 39.3 mmol) in methanol (50 mL) was added thionyl chloride (6 mL, 78.6 mmol) drop wise under stirring at rt. The reaction mixture was refluxed for 2 h and attained to rt. The mixture was poured into ice cooled water and stirred for 15 min. The precipitated solid was filtered, washed with cold water and dried to give the product as an off-white solid (6.2 g, 85%). $^1$H NMR showed that, it is a mixture of two compounds and the crude product was proceded to the next step.

Step c:

Methyl 4-aminothiophene-2-carboxylate: To a solution of methyl nitrothiophene-2-carboxylates (7 g, 37.43 mmol) in a mixture of water (150 mL) and methanol (50 mL) was added Conc. hydrochloric acid (4.5 mL). To the above solution was added iron powder (10.5 g, 188 mmol) followed by ammonium chloride (10 g, 187 mmol) at rt. The reaction mixture was stirred and warmed to 70° C. for 1 h and was then allowed to cool to rt. The solution was filtered and basified with saturated sodium bicarbonate solution. The solution was extracted with chloroform (4×100 mL). The combined organic layer was dried over sodium sulfate and filtered. Solvent was evaporated and the residue was chromatographed over silica gel column using hexane-ethyl acetate (90:10 and small amount of triethyl amine) as eluent to give methyl 4-aminothiophene-2-carboxylate (1.8 g, 31%), mp 76-78° C. $^1$H NMR (400 MHz, CDCl$_3$): δ 7.31 (1H, d, J=1.6 Hz), 6.40 (1H, d, J=1.6 Hz), 3.85 (3H, s), 3.63 (2H, br s). Further elution of the column with the same solvent system provided methyl 5-aminothiophene-2-carboxylate (0.5 g, 8.5%), mp 70-72° C. $^1$H NMR (400 MHz, CDCl$_3$): δ 7.45 (1H, d, J=4.0 Hz), 6.09 (1H, d, J=4.0 Hz), 4.29 (2H, br s), 3.81 (3H, s).

Step d:
Methyl 4-[(dimethylamino)diazenyl]thiophene-2-carboxylate: To a solution of methyl 4-aminothiophene-2-carboxylate (1.7 g, 10.82 mmol) and conc. HCl (4.6 mL, 43.5 mmol) in H$_2$O (20 mL) was added NaNO$_2$ (0.84 g, 12.17 mmol) in portions for 5 min at 0° C. After stirring for 0.5 h at 0-5° C., the reaction mixture was added to the solution of K$_2$CO$_3$ (5.8 g, 42 mmol) and dimethylamine (4.6 mL, 40%, 40.9 mmol) in H$_2$O (30 mL) at 0° C. The mixture was stirred at 0-5° C. for 1 h and poured into ice cold water. The solution was extracted with chloroform (3×100 mL). The combined CHCl$_3$ layer was washed with water, brine and dried over sodium sulfate. The solution was filtered and evaporated the solvent. The residue was chromatographed over silica gel column using hexane-EtOAc (80:20) as eluents to give the product as light red color solid (250 mg), which was recrystallized from chloroform-hexane (110 mg), mp 90-92° C. $^1$H NMR (400 MHz, CDCl$_3$): δ 7.93 (1H, d, J=1.6 Hz), 7.31 (1H, d, J=1.6 Hz), 3.88 (3H, s), 3.31 (6H, br s).

Step e:
4-[Dimethylamino)diazenyl]thiophene-2-carboxamide: To an ice cold (0-5° C.) solution of ammonium hydroxide (5 mL) was added a solution of methyl 4-[(dimethylamino)diazenyl]thiophene-2-carboxylate (110 mg) in THF (2 mL) for 5 min and stirred at rt for 20 h. The solution was poured into ice cooled water and extracted with chloroform. The combined organic layer was washed with water, brine and dried over sodium sulfate. The solution was filtered and evaporated the solvent. The residue was chromatographed over silica gel column using chloroform-methanol (99:1) as eluents to give the product as pale red color solid (60 mg, 60%), mp 128-130° C. IR (neat) ν$_{max}$ 3372, 3189, 1648, 1609, 1219, 1120, 1088, 865, 772 cm$^{-1}$; $^1$H NMR (400 MHz, CDCl$_3$): δ 7.68 (1H, d, J=1.2 Hz), 7.28 (1H, d, J=1.2 Hz), 6.18 (2H, br s), 3.29 (6H, br s); LC-MS (positive ion mode): m/z 199 (M+H)$^+$.

Example 13

Synthesis of 4-[(dimethylamino)diazenyl]thiophene-3-carboxamide (Compound 13)

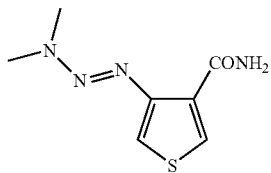

Step a:
Methyl 3-[(methoxycarbonyl)methylthio]propanoate: Methyl acrylate (4.25 g, 49.5 mmol) was added dropwise over 20 min to a stirred solution of methyl thioglycolate (5 g, 47.16 mmol) and piperidine (0.10 mL) at rt. When about half of the acrylate had been introduced, more piperidine (0.10 mL) was added. After completion of the addition of the acrylate, the reaction mixture was stirred for 1 h at rt. The mixture was diluted with 100 mL of chloroform. The chloroform layer was washed with water, brine and dried over Na$_2$SO$_4$. The solution was filtered and evaporated the solvent to give the product as an oil (9 g, 100%).

Step b:
Methyl 4-oxo-2,3,5-trihydrothiophene-3-carboxylate: To a stirred slurry of sodium methoxide (1.68 g, 31.25 mmol) in dry THF (15 mL) was added a solution of dimethyl 3-thiahexanedioate (5 g, 26.03 mmol) in THF (10 mL) at rt for 5 min. The reaction mixture was heated at reflux for 2 h, cooled to rt and poured into ice cold water and acidified with dil. HCl. The solution was extracted with chloroform and the combined chloroform layer was washed with water, brine and dried over sodium sulfate. The solution was filtered and evaporated the solvent. The residue was chromatographed over silica gel column using hexane-EtOAc (95:5) as eluents to give the product as pale yellow color oil (1.6 g, 39%).

Step c:
Methyl 4-aminothiophene-3-carboxylate hydrochloride: A mixture of 4-oxo-3-methoxycarbonyltetrahydrothiophene (6.5 g, 40.62 mmol), hydroxylamine hydrochloride (2.84 g, 40.62 mmol) and acetonitrile (30 mL) was stirred under reflux for 1 h. The mixture was then cooled and the solid which separated was filtered off and washed with dry ether to afford the title compound (4.9 g, 62%), mp 192-196° C.

Step d:
Methyl 4-aminothiophene-3-carboxylate: Methyl 4-aminothiophene-3-carboxylate hydrochloride (290 mg) was dissolved in water (20 mL) and basified with ammonia solution. The solution was extracted with chloroform and the combined chloroform layer was washed with water, brine and dried over sodium sulfate. The solution was filtered and evaporated the solvent to give the product as pale yellow color oil (150 mg, 65%). $^1$H NMR (400 MHz, CDCl$_3$): δ 7.92 (1H, d, J=3.6 Hz), 6.08 (1H, d, J=3.6 Hz), 4.79 (2H, br s), 3.85 (3H, s).

Step e:
Methyl 4-[(dimethylamino)diazenyl]thiophene-3-carboxylate: To a solution of methyl 4-aminothiophene-3-carboxylate (200 mg, 1.27 mmol) and conc. HCl (0.5 mL, 5.09 mmol) in H$_2$O (5 mL) was added NaNO$_2$ (96 mg, 1.39 mmol) in portions for 5 min at 0° C. After stirring for 0.5 h at 0-5° C., the reaction mixture was added to the solution of K$_2$CO$_3$ (665 mg, 4.8 mmol) and dimethylamine (0.5 mL, 40%, 4.57 mmol) in H$_2$O (5 mL) at 0° C. The mixture was stirred at 0-5° C. for 1 h and poured into ice cold water. The solution was extracted with chloroform (3×30 mL). The combined CHCl$_3$ layer was washed with water, brine and dried over sodium sulfate. The solution was filtered and evaporated the solvent. The residue was chromatographed over silica gel column using hexane-EtOAc (90:10) as eluents to give the product as pale red color oil (20 mg, 8%). $^1$H NMR (400 MHz, CDCl$_3$): δ 8.00 (1H, d, J=2.8 Hz), 6.97 (1H, d, J=3.6 Hz), 3.85 (3H, s), 3.34 (6H, br s).

Step f:
4-[(Dimethylamino)diazenyl]thiophene-3-carboxamide: To an ice cold (0-5° C.) solution of ammonium hydroxide (5 mL) was added a solution of methyl 4-[(dimethylamino)diazenyl]thiophene-3-carboxylate (110 mg) in THF (2 mL) for 5 min and stirred at rt for 36 h. The solution was poured into ice cooled water and extracted with chloroform. The combined chloroform layer was washed with water, brine and dried over sodium sulfate. The solution was filtered and evaporated the solvent. The residue was chromatographed over silica gel column using chloroform-methanol (98:2) as eluents to give the product as a pale red color solid (25 mg, 25%), mp 168-172° C. IR (neat) $v_{max}$ 3324, 3125, 2917, 2851, 1655, 1600, 1367, 1336, 1090 cm$^{-1}$; $^1$H NMR (400 MHz, CDCl$_3$): δ 8.55 (1H, br s), 8.19 (1H, d, J=3.6 Hz), 7.15 (1H, d, J=3.6 Hz), 5.84 (1H, br s), 3.56 (3H, br s), 3.19 (3H, br s); LC-MS (positive ion mode): m/z 199 (M+H)$^+$.

Example 14

Synthesis of potassium salt of 3-[(dimethylamino)diazenyl]thiophene-2-carboxylic acid (Compound 14)

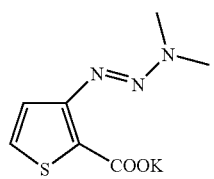

To a solution of 3-[(dimethylamino)diazenyl]thiophene-2-carboxylic acid (example 4: 300 mg, 1.50 mmol) in methanol (15 mL) was added a solution of potassium hydroxide (84 mg, 1.50 mmol) in methanol (5 mL) at rt and the mixture stirred at the same temperature for 1 h. The solution was filtered to remove any impurities and evaporated under reduced pressure to get the compound as a brown color solid (290 mg, 81%), mp 274-280° C. $^1$H NMR (400 MHz, D$_2$O): δ 7.36 (1H, d, J=5.6 Hz), 7.10 (1H, d, J=5.6 Hz); LC-MS (positive ion mode): m/z 238 (M+H)$^+$.

Example 15

Synthesis of 3-methylthiopheno[2,3-d]-1,2,3-triazin-4-one (Compound 15)

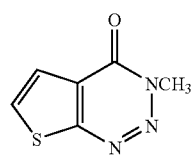

Step a:

2-Aminothiophene-3-carboxamide: To a solution of 2,5-dihydroxy-1,4-dithiane (10 g, 65.78 mmol) in ethanol (200 mL) and triethylamine (2 mL) was added cyanoacetamide (5.52 g, 65.78 mmol) at rt for 5 min. The reaction mixture was refluxed for 3 h and attained to rt. Ethanol (appr. 150 mL) was removed under reduced pressure and poured the contents into ice cold water and stirred for 15 min. The solution was extracted with ethyl acetate (3×100 mL) and the combined EtOAc layer was washed with water, brine and dried over sodium sulfate. The solution was filtered and evaporated the solvent. The residue was chromatographed over silica gel column using chloroform-methanol (95:5) as eluents to give the product as a pale yellow color solid (4.9 g, 53%), mp 150-152° C.

Step b:

3H-Thiopheno[2,3-d]1,2,3-triazin-4-one: To an ice cold solution (0° C.) of 2-aminothiophene-3-carboxamide (5 g, 35.21 mmol) in concentrated sulfuric acid (40 mL) was added a cold (0° C.) solution of sodium nitrite (2.5 g, 35.21 mmol) in concentrated sulfuric acid (30 mL) for 30 min (while adding, the temperature should keep between −5-0° C.). After addition, the mixture was stirred at the same temperature (0° C.) for 3 h. The mixture was poured into crushed ice slowly with stirring for 15 min and stirred at the same temperature for 15 min. The solution was extracted with ethyl acetate (4×200 mL) and the combined EtOAc layer was washed with water, brine and dried over sodium sulfate. The solution was filtered and evaporated the solvent. The residue was chromatographed over silica gel column using chloroform-methanol (95:5) as eluents to give the product as a pale red color solid (1.0 g, 18%), mp 175-176° C. $^1$H NMR (400 MHz, DMSO-d$_6$): δ 15.18 (1H, s), 8.16 (1H, d, J=5.6 Hz), 7.64 (1H, d, J=5.6 Hz); $^{13}$C NMR (100 MHz, DMSO-d$_6$): δ 159.1, 153.8, 132.0, 126.1, 121.2; LC-MS (negative ion mode): m/z 152 (M−H)$^-$.

Step c:

3-Methylthiopheno[2,3-d]1,2,3-triazin-4-one: To a solution of 3H-thiopheno[2,3-d]1,2,3-triazin-4-one (80 mg, 0.522 mmol) in acetone (50 mL) was added sequentially potassium carbonate (144 mg, 1.04 mmol), iodomethane (0.04 mL, 0.627 mmol) and potassium iodide (catalytic) at rt and the mixture was stirred at rt for 3 h. The solution was filtered and the solids were washed with acetone. Acetone was evaporated under reduced pressure, diluted with ice cold water and stirred for 10 min. The solution was extracted with chloroform (4×75 mL) and the combined CHCl$_3$ layer was washed with water, brine and dried over sodium sulfate. The solution was filtered and evaporated the solvent. The residue was chromatographed over silica gel column using hexane-ethyl acetate (90:10) as eluents to give the product as an off-white solid (50 mg, 57%), mp 104-108° C. $^1$H NMR (400 MHz, DMSO-d$_6$): δ 8.17 (1H, d, J=5.6 Hz), 7.64 (1H, d, J=5.6 Hz), 3.95 (3H, s); $^{13}$C NMR (100 MHz, CDCl$_3$): δ 159.4, 153.9, 130.7, 125.6, 121.7, 37.3.

Example 16

Synthesis of 3-methyl-6-nitrothiopheno[2,3-d]1,2,3-triazin-4-one (Compound 16)

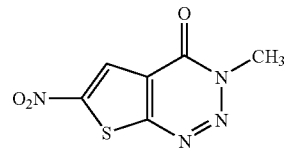

To an ice cold (−10° C.) solution of concentrated sulfuric acid (5 mL) was added 3-methylthiopheno[2,3-d]1,2,3-triazin-4-one (0.6 g, 3.6 mmol) for 10 min., nitric acid (0.4 mL, 9 mmol) was added to the above reaction mixture for 5 min and the mixture was attained to rt and stirred for 1 h. The mixture was poured into ice cold water and stirred for 15 min. The precipitated solid was filtered and purified by silica gel column chromatography using hexane-chloroform (1:1) as eluents to give the product as a pale yellow color solid (390 mg, 51%), mp 164-168° C. $^1$H NMR (400 MHz, DMSO-d$_6$): δ 8.60 (1H, s), 3.99 (3H, s).

Example 17

Synthesis of 6-amino-3-methylthiopheno[2,3-d]1,2,3-triazin-4-one (Compound 17)

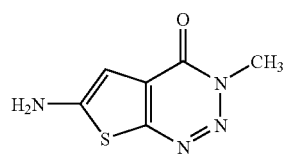

To a solution of 3-methyl-6-nitrothiopheno[2,3-d]1,2,3-triazin-4-one (1.25 g, 5.9 mmol) in methanol (50 mL) was added conc. Hydrochloric acid (0.6 mL). To the above solution was added iron powder (1.67 g, 29.5 mmol) followed by a solution of ammonium chloride (1.57 g, 29.5 mmol) in water (10 mL) at rt. The reaction mixture was stirred and warmed to 70 for 1 h and was then allowed to cool to rt. The solution was filtered and basified with saturated sodium bicarbonate solution. The solution was extracted with ethyl acetate (4×100 mL). The combined organic layer was dried over sodium sulfate and filtered. Solvent was evaporated and the residue was chromatographed over silica gel column using hexane-ethyl: acetate (60:40) as eluents to give the product as a pale yellow color solid (80 mg, 7.5%), mp 190-194° C. $^1$H NMR (400 MHz, DMSO-d$_6$): δ 7.40 (2H, s), 6.11 (1H, s), 3.82 (3H, s); LC-MS (negative ion mode): m/z 181 (M−H)$^-$.

Example 18

Synthesis of 3-methyl-6-phenylthiopheno[3,2-d]1,2,3-triazin-4-one (Compound 18)

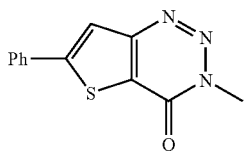

Step a:
3-Amino-5-phenylthiophene-2-carbonitrile: To a suspension of sodium sulfide (0.95 g, 12.23 mmol) in DMF (12.5 mL) was added a solution of 3-chloro-3-phenylprop-2-enenitrile (2 g, 12.23 mmol) in DMF (5 mL) at rt for 5 min and stirred the mixture at 60-70° C. for 2 h. Then chloroacetonitrile (0.77 mL, 12.23 mmol) was added dropwise to the reaction mixture and again stirred at 60-70° C. for 2 h. Then, a solution of sodium methoxide (0.66 g, 12.23 mmol) in methanol (5 mL) was added dropwise and stirring was continued for 1 h at the same temperature. The mixture was allowed to rt and poured into cold water and stirred for 15 min. The solid separated was filtered, washed with water and dried. The solid was recrystallized from hexane-chloroform to give the product as a pale brown color solid (150 mg, 8%), nip 158-160° C. $^1$H NMR (400 MHz, CDCl$_3$): δ 7.52-7.54 (2H, m), 7.37-7.41 (3H, m), 6.75 (1H, s), 4.48 (2H, s); LC-MS (negative ion mode): m/z 199 (M−H)$^-$.

Step b:
3-Amino-5-phenylthiophene-2-carboxamide: To a suspension of 3-amino-5-phenylthiophene-2-carbonitrile (150 mg) in aqueous sodium hydroxide solution (20 mL, 10%) was added ethanol (10 mL) and the mixture was refluxed for 1 h. The reaction mixture was allowed to attain rt and the crystals separated were filtered off, washed with cold water and dried to give the product as a golden yellow color solid (70 mg, 45%), mp 180-182° C.
$^1$H NMR (400 MHz, CDCl$_3$): δ 7.56-7.58 (2H, m), 7.33-7.41 (3H, m), 6.79 (1H, s), 5.68 (1H, s), 5.21 (1H, s); LC-MS (positive ion mode): m/z 241 (M+Na)$^+$.

Step c:
6-Phenyl-3H-thiopheno[3,2-d]1,2,3-triazin-4-one: To an ice cold solution (0° C.) of 3-amino-5-phenylthiophene-2-carboxamide (0.37 g, 1.7 mmol) in concentrated sulfuric acid (20 mL) was added a cold (0° C.) solution of sodium nitrite (120 mg, 1.86 mmol) in concentrated sulfuric acid (8 mL) for 10 min (while adding, the temperature should keep between −5-0° C.). After addition, the mixture was stirred at 0° C. for 1 h and at rt for 1 h. The reaction mixture was cooled and poured into crushed ice slowly with stirring for 15 min and stirred at the same temperature for 15 min. The solution was extracted with ethyl acetate (3×50 mL) and the combined EtOAc layer was washed with water, brine and dried over sodium sulfate. The solution was filtered and evaporated the solvent to give the product as an off-white color solid (200 mg, 39%), my 178-180° C. $^1$H NMR (400 MHz, CDCl$_3$): δ 12.30 (1H, br s), 7.86 (1H, s), 7.73-7.75 (2H, m), 7.49-7.54 (3H, m); LC-MS (negative ion mode): m/z 228 (M−H)$^-$.

Step d:
3-Methyl-6-phenylthiopheno[3,2-d]1,2,3-triazin-4-one:
To a solution of 6-phenyl-3H-thiopheno[3,2-d]1,2,3-triazin-4-one (250 mg, 1.1 mmol) in acetone (25 mL) was added sequentially potassium carbonate (300 mg, 2.18 mmol), iodomethane (0.08 mL, 1.31 mmol) and potassium iodide (catalytic) at rt and the mixture was stirred at rt for 16 h. The solution was filtered and the solids were washed with acetone. Acetone was evaporated under reduced pressure, diluted with ice cold water and stirred for 10 min. The solution was extracted with chloroform (4×75 mL) and the combined CHCl$_3$ layer was washed with water, brine and dried over sodium sulfate. The solution was filtered and evaporated the solvent. The residue was chromatographed over silica gel column using chloroform-methanol (95:05) as eluents to give the product as a yellow color solid (110 mg, 42%), mp 220-222° C. IR (KBr) $v_{max}$ 3095, 2924, 1680, 1298, 1248, 1102, 977, 829 cm$^{-1}$; $^1$H NMR (400 MHz, CDCl$_3$): δ 7.78 (1H, s), 7.70-7.73 (2H, m), 7.45-7.51 (3H, m), 4.09 (3H, s); $^{13}$C NMR (100 MHz, CDCl$_3$): δ 155.1, 153.8, 153.3, 132.2, 130.2, 129.4, 126.7, 125.4, 119.5, 37.4; LC-MS (positive ion mode): m/z 244 (M+H)$^+$.

Evaluation of Anti-Melanoma Tumor Growth Potential in In Vitro and In Vivo

Example 19

Cell Proliferation Assay Using MTT Based Assay

MTT [3-(4,5-dimethylthiazol-2-yl)-2,5-diphenyltetrazolium bromide] incorporation based cell proliferation assay was performed using standard procedure with some modifications (38). The cytotoxic efficacy of the test compounds were evaluated in human malignant melanoma A2058 cells by MTT cell proliferation assay kit (Roche Applied Sciences, Germany). The assay was carried out according to the instruction provided by the vendor. Briefly, equal numbers of cells was plated in 96-well flat-bottomed plates in 100 μl of medium and were exposed to either DTIC or its derivative compounds at various concentrations up to 150 μg/ml for a period of three days. Vehicle control culture wells received only a maximum of 0.5% DMSO. Thereafter, 0.5 mg/ml of MTT reagent was added to each well and the microplate was incubated further for 4 h at 37° C. in presence of 5% $CO_2$. Finally, the cells were solubilized by adding solubilizing solution and allowed to incubate at 37° C. overnight. After complete solubilization of the formazan crystals the absorbance was read at 540 nm in a microplate reader (BioRad, USA). The results (mean OD±SD) obtained from quadruplicate wells were used in calculation to determine the inhibition of cell proliferation (50% inhibitory concentration, $IC_{50}$) of the test compounds.

TABLE 1

Anti-tumor potential of DTIC and its related compounds in A2058, human malignant melanoma cells

| Test compounds | $IC_{50}$ in A2058 cells (μg/mL) |
|---|---|
| Compound 1 | 78.701 |
| Compound 2 | 113.3 |
| Compound 6 | 53.6 |
| Compound 9 | 214.2 |
| Compound 10 | 178.7 |
| Compound 11 | 164.3 |
| Compound 12 | 165.01 |
| Compound 13 | 48.8 |
| Compound 17 | 146.7 |
| DTIC | 68.08 |

Example 20

Cytotoxicity Using LDH Leakage Assay

From the data obtained from the MTT assay (Table J), compound 1, compound 6 and compound 13 have been selected and their cytotoxicity potential has been further validated in LDH leakage assay. FIG. 1 shows loss of cell viability in terms of percent increase in leaked LDH at different concentrations of DTIC and other test compounds as indicated. Cytotoxicity potential of DTIC and its derivative compounds were evaluated by measuring the leaked lactate dehydrogenase (LDH) into the culture supernatant (LDH Cytotoxicity Detection Roche Applied Sciences, Germany). The leaked LDH is directly proportional to the cell damage done by the cytotoxic compounds. In brief, cells were treated with test compounds at various concentrations and incubated for 48 h. Vehicle control culture wells received only a maximum of 0.5% DMSO. The cell free culture supernatants were mixed with catalyst and dye solution and allowed to incubate for 15 min at room temperature. Finally, the reaction was stopped and the optical density was measured at 492 nm in a microplate reader (BioRad, USA). The results (mean OD±SD) obtained from quadruplicate wells were used in calculation to determine the cytotoxicity potential (50% of inhibitory concentration, $IC_{50}$) of the test compounds. A plot of loss of cell viability as indicated by the leakage of LDH versus drug concentration is depicted in FIG. 1.

Example 21

Tumor Selectivity

Figure 2:
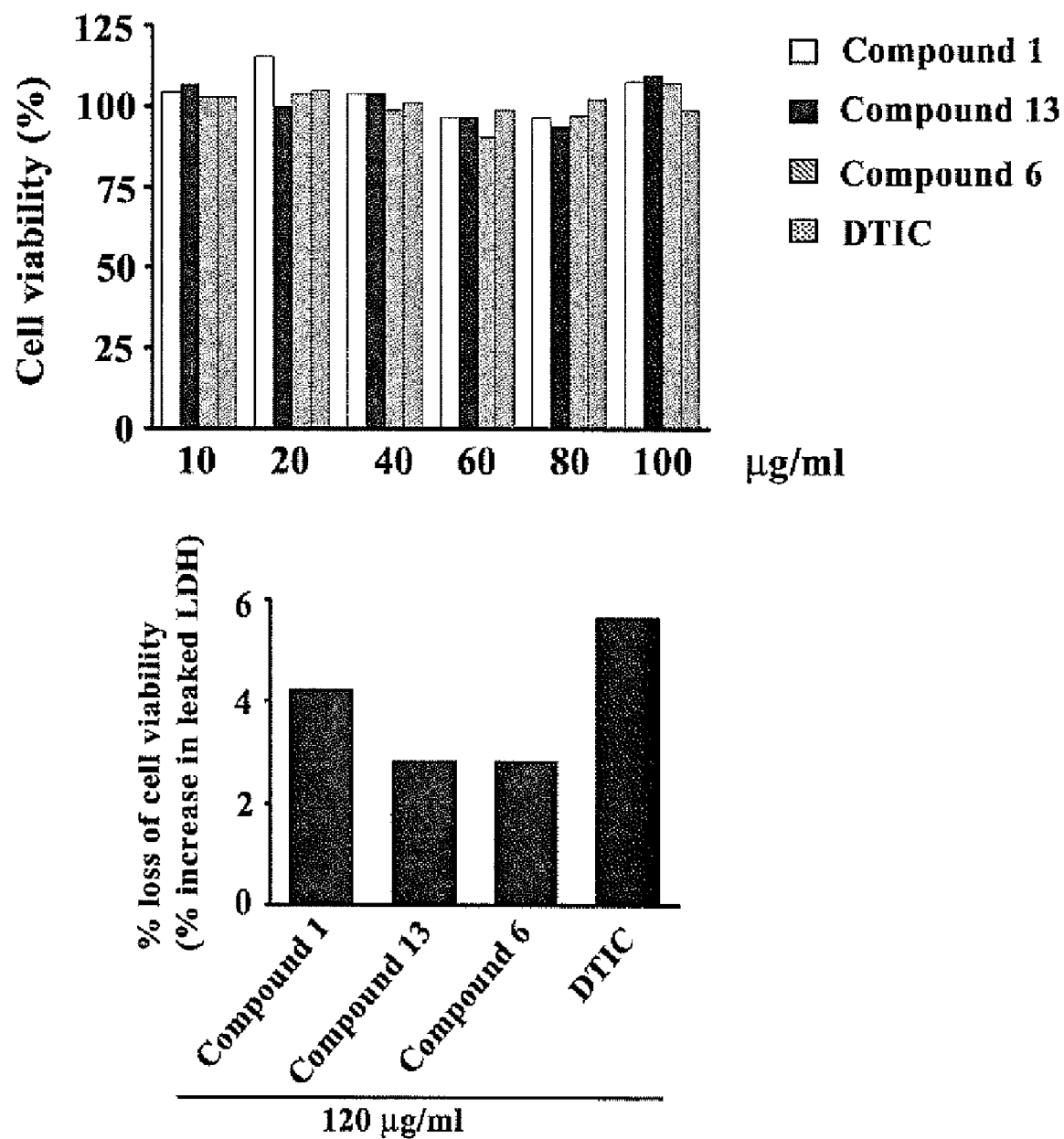
FIG. 2 illustrates bar diagrammatic representation of percent of cell viability of HS.531.sk normal human skin epithelial cells treated with different concentrations of DTIC and related test compounds (upper panel). Bar diagram at the lower panel represents the loss (in percentage) of HS.531.sk cell viability by various test compounds at 120 µg/ml as indicated.

Next, to check whether the DTIC derivative compounds can selectively kill the melanoma cells without or minimally affecting the normal cells, we assessed the effect of the test compounds on normal human skin epithelial HS.531.sk cells. LDH leakage assay indicate that up to 100 μg/ml dose of DTIC and its derivative compounds do not affect the normal cell skin cell growth. Whereas, 120 μg/ml of DTIC, compound 1, compound 3 and compound 4 caused 5.8%, 4.2%, 2.4%, and 2.4% reduction in normal cell viability, respectively. Therefore, from this observation it is evident that compound 3 and compound 4 possess more selectivity than DTIC to kill melanoma cells without or minimally affecting the normal cells (FIG. 2).

Example 22

Figure 3:
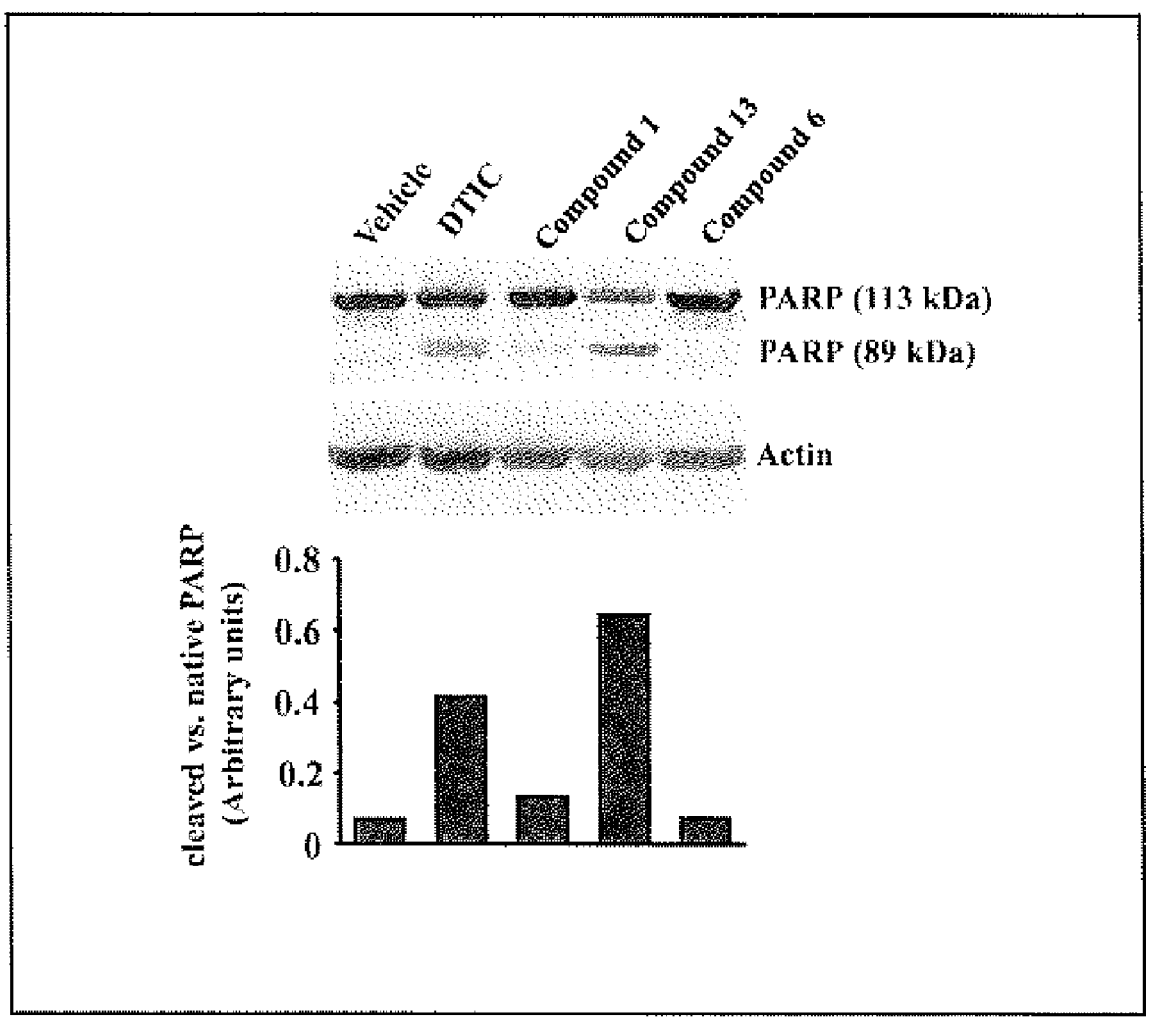
FIG. 3 illustrates Western immunoblot image represents PARP cleavage in A2058 cells treated with 100 µg/ml of DTIC and test products Compound 1, Compound 6, and Compound 13. Control cultures received 0.5% DMSO as a vehicle. Expression of actin protein is shown as the loading control. Expression of the cleaved PARP protein at 89 kDa was normalized with actin expression (in arbitrary units), and represented as a bar diagram in the lower panel.

Effect of the Triazene Compounds on the Apoptotic Cell Death Potential in A2058 Human Melanoma Cells Proteolytic cleavage of PARP by caspases is regarded as a hallmark of apoptosis. Caspase-3 cleaves the 113-kDa PARP to generate 89- and 24-kDa polypeptides (39). Next, with an intention to evaluate the comparative apoptotic potential of DTIC and test products compound 1, compound 6 and compound 13, PARP cleavage assay has been performed on A2058 cells. PARP cleavage was estimated by using Western immunoblot assay as described earlier (40). FIG. 3 illustrates comparative efficacy of PARP cleavage by the test compounds at a fixed dose of 100 μg/ml. Western blot image shows the expression of cleaved subunit of PARP at 89 kDa in compd. No. 3 treated A2058 cells is 56.6% more than in DTIC treated cells at the same concentration. This observation suggests that compd. No. 3 exhibits better apoptotic cell death potential in A2058 human melanoma cells Example 23

Comparative Efficacy of Cell Proliferation Inhibition by DTIC And Compound 6 in B16F0 Mouse Melanoma Cells and A375 Human Melanoma Cells The comparative anti-tumor growth potential of DTIC and Compound 6 was further tested in B16F0 mouse melanoma cells and A375 human melanoma cells by using MTT based cell proliferation assay following the methodology described earlier (Example 19). Briefly, equal numbers of either B16F0 or A375 cells were plated in 96-well flat-bottomed plates in 100 of medium and were treated with either DTIC or Compound 6 at different concentrations for 3 days. Vehicle control culture wells received only a maximum of 0.5% DMSO. After adding the MTT reagent, the cells were solubilized and the intracellular formazan formation was calorimetrically read at 540 nm in a microplate reader (BioRad, USA). The results (mean OD±SD) obtained from quadruplicate wells were used in calculation to determine the inhibition of cell proliferation (50% of inhibitory concentration, IC50) of the test compounds.

TABLE 2

Comparative anti-tumor growth potential of DTIC and Compound 6 in B16F0 mouse melanoma and A375 human melanoma cells

| Test compounds | 50% of inhibitory concentration, IC50 (μg/ml) in | |
|---|---|---|
| | B16 F0 cells | A375 cells |
| DTIC | 360.4 | 70.1 |
| Compound 6 | 57.6 | 46.5 |

Example 24

Comparative Cytotoxicity Potential of DTIC and Compound 6 On B16F0 Mouse Melanoma Cells and A375 Human Melanoma Cells Comparative cytotoxicity potential of DTIC and Compound 6 on B16F0 mouse melanoma cells and A375 human melanoma cells were further evaluated by measuring the leaked lactate dehydrogenase (LDH) into the culture supernatant (LDH Cytotoxicity Detection Kit$^{Plus}$, Roche Applied Sciences, Germany), following the methodology described earlier (Example 20). The results (mean OD±SD) obtained from quadruplicate wells were used in calculation to determine the cytotoxicity potential (50% of inhibitory concentration, IC50) of the test compounds (Table 3).

TABLE 3

Comparative cytotoxicity potential of DTIC and compound 6 in B16F0 mouse melanoma and A375 human melanoma cells

| Test compounds | Treatment concentration (µg/ml) | % increase in LDH secretion with respect to vehicle treated control in | |
|---|---|---|---|
| | | B16 F0 cells | A375 cells |
| DTIC | 100 | 5.7 | 246 |
| Compound 6 | 100 | 61.5 | 331 |

Example 25

Anti-Tumor Efficacy of Compound 1 and Compound 6 in MCF-7 Human Breast Tumor Cells, MIA-PaCa2 Human Pancreas Tumor Cells and DU145 Human Prostate Tumor Cells Anti-tumor growth potential of Compound 1 and Compound 6 were evaluated in MCF-7 human breast tumor cells, MIA-PaCa2 human pancreas tumor cells and DU145 human prostate tumor cells by using MTT based cell proliferation studies as described earlier (example 19). The results (mean OD±SD) obtained from quadruplicate wells were used in calculation to determine the inhibition of cell proliferation (50% of inhibitory concentration, IC50) of the test compounds (Table 4).

TABLE 4

Comparative anti-tumor growth potentials of DTIC, Compound 1 and Compound 6 in MCF-7 human breast tumor cells, MIA-PaCa2 human pancreas tumor cells and DU145 human prostate tumor cells

| Test compounds | 50% of inhibitory concentration, IC50 (µg/ml) | | |
|---|---|---|---|
| | MCF-7 | MIA-PaCa2 | DU145 |
| DTIC | 135.1 | 202.9 | 87.2 |
| Compound 1 | 130.3 | 168.5 | 153.2 |
| Compound 6 | 91.7 | 81.9 | 62.6 |

Example 26

B16 F0 Mouse Melanoma Cell Colony Formation Assay

Clone formation efficiency of the Compound 6 and DTIC was tested by following the procedure described earlier with some modifications (41). Briefly, B16F0 cells were harvested and seeded into 6-well plates (100 cells/ml). The cells were allowed to grow for 2 days and thereafter, the cells were incubated with DMEM containing either 0.1% DMSO or 100 µg/ml DTIC or 50 µg/ml and 100 µg/ml of Compound 6 for further 8 days. Fresh medium containing test agents was replaced at every 24 h. Finally, the wells were washed three times with PBS and fixed in methanol for 15 min. The cells were stained with Giemsa stain and observed under microscope. The image of the stained wells were captured digitally (Kodak Image Station 4000MM, Carestream Health Inc., New Haven, Conn.) and number of colonies were counted and analyzed by using NIH Image J software. FIG. 4 shows inhibition of B16 colony growth in DTIC and Compound 6 treated wells. Compound 6 exhibited significant inhibition in B16 tumor cell colony growth compared with DTIC. 37.6%, 55.2% and 68.7% growth inhibitions were achieved by 100 µg/ml of DTIC, 50 µg/ml and 100 µg/ml of Compound 6, respectively.

Example 27

Cell Cycle Analysis of Compound 6 Treated B16 F0 Mouse Melanoma Cells

Figure 5:
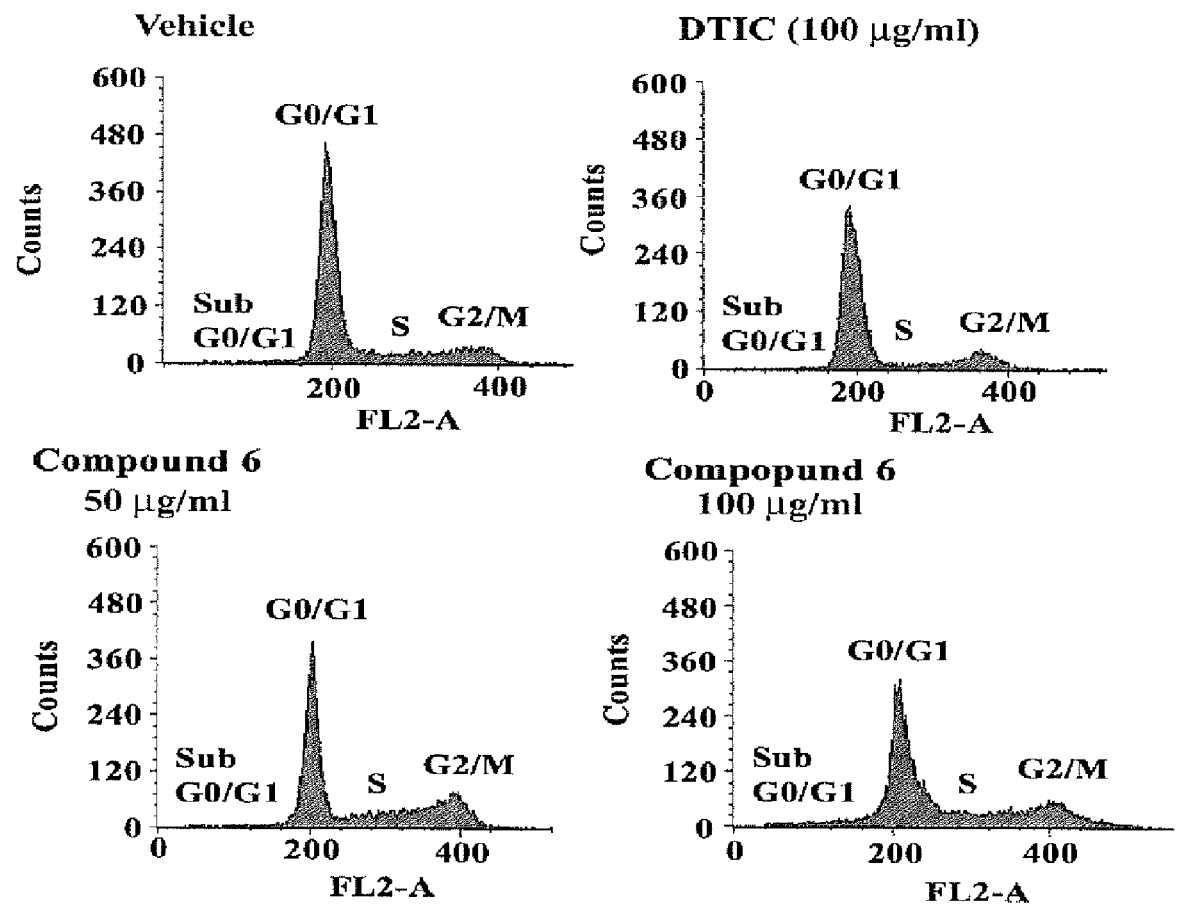
FIG. 5 represents induction of cell cycle arrest in G2/M phase by Compound 6. B16 F0 Cells were treated with the indicated concentrations of either vehicle (0.1% DMSO) or DTIC or Compound 6 for 24 h at different concentrations as indicated. The propidium iodide stained cells were analyzed for the distribution of cell cycle by FACS calibur, and the percentage of distribution at different phases of cell cycle was determined using ModFIT software. Data are shown as one representative of at least three independent experiments.

Cell cycle analysis of Compound 6 and DTIC treated B16F0 cells were analyzed by flow cytometry as described earlier with some modifications (42). Briefly, B16F0 cells were cultivated in DMEM containing 10% fetal bovine serum (FBS) in presence of 4.5 g/l D-glucose. The sub confluent cells were treated with either DTIC or Compound 6 and incubated for 24 h. Cells were harvested and prepared single cell suspension in buffer (PBS+2% FBS). The cells were washed twice with cold PBS and then fixed with cold 70% ethanol for 30 min. Ethanol was removed by centrifugation and the cells were suspended and the cell count was adjusted to $10^6$ cells per ml. The cells were washed two times with PBS and then the cells were stained with propidium iodide for 30 min at 37° C. in presence of RNase. Finally, the cells were analyzed on FACS Calibur flow cytometry (BD Biosciences, USA). FIG. 5 depicts the distribution of cells in different phases of cell cycle modulated by DTIC and Compound 6.

Example 28

B16F0 Mouse Melanoma Cell Invasion Assay

Figure 6:
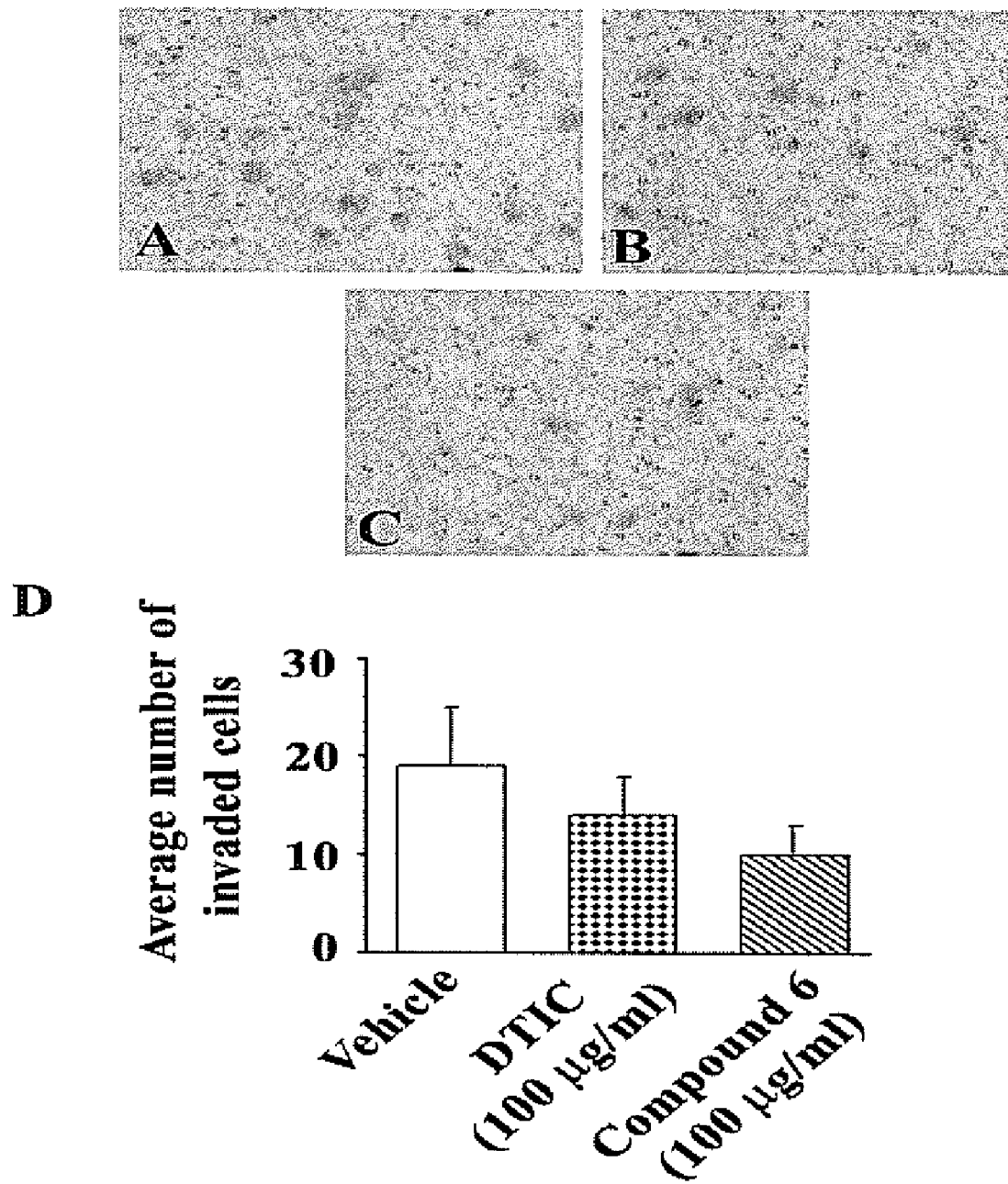
FIG. 6 represents photomicrographs showing invaded B16F0 cells in control (A), 100 µg/ml of DTIC (B), and Compound 6 (C) treated cultures. Bar diagram (D) represents the average number of invaded cells counted from 20 independent fields observed at 20× objective.

The inhibitory effects of DTIC and compound 4 on In vitro invasive ability of B16F0 were tested in cell invasion assay performed with by using Matrigel (BME Cultrex®, R&D Systems, USA) coated cell culture inserts (Becton Dickinson, USA) with 8 µm-pore membrane. Equal number (fifty thousands) of B16F0 cells were applied in each insert well and allowed to attach for 2 h at 37° C. and in presence of 5% $CO_2$. Thereafter, the cellular invasion through the matrigel layer was performed in presence or absence of test compounds. Either 100 µg/ml of DTIC or Compound 6 was applied in the lower chamber of the invasion assembly. 0.1% DMSO was applied in the vehicle control culture chambers. After 24 h treatment, the matrigel layer containing cells was removed with cotton plug and the invaded cells on the other side of the membrane were fixed with methanol for 5 min and then stained with Giemsa. The stained membrane was mounted on a glass slide and number invaded cells were counted in 20 random fields (20× objective) under a light microscope (Nikon Eclipse TS 100). Compound 6 significantly reduced malignant tumor cell invasion when compared to vehicle or DTIC in in vitro B16 melanoma cell culture experiment (FIG. 6).

Example 29

Compound 6 Inhibits Vascular Endothelial Growth Factor (VEGF) production B16F0 cells B16F0 cells were cultivated in Dulbecco's modified Eagle's red medium (DMEM) (Sigma Life Science, USA) containing 10% fetal bovine serum (FBS) and 4.5 g/l D-glucose. Equal number cells ($5 \times 10^4$) were seeded in culture dishes (35×10 mm, 11.7 $cm^2$). The cells were treated with either 50 μg/ml of DTIC or Compound 4 for 24 h. The cells incubated with only 0.1% DMSO was considered as vehicle control. After 24 h, the cell lysates were prepared and analyzed for Vascular Endothelial Growth Factor (VEGF) expression by western blot assay as described earlier with appropriate modifications (43).
For Western blot analyses, equal amount of B16F0 cell lysate proteins were separated in 12.5% SDS-PAGE under reducing conditions, and transferred onto nitrocellulose membranes (Bio-Rad, USA). The membranes were blocked with SuperBlock (Thermo scientific, USA) and subsequently reacted with VEGF antibody (Abcam, UK) at 4° C. overnight. Bound antibodies were probed with horseradish peroxidase conjugated secondary antibody and the specific immunoreactions were developed with enhanced chemiluminescence (Thermo scientific, USA). The stripped membranes were developed again with anti-actin antibody as an internal loading control. The images of immunoreactive bands were captured in Kodak Image Station 4000MM (Carestream Health Inc., New Haven, Conn.) and analyzed densitometrically by Kodak molecular Imaging software, Version 4.5. FIG. 7 depicts a representative immunoblot image shows down regulation of VEGF protein in Compound 6 treated B16F0 cells.

Example 30

Endothelial Cell Migration Assay

The methodology of endothelial cell migration assay was essentially the same as described earlier with some modifications (43). FALCON™ Cell Culture inserts (Becton Dickinson, USA) with 8 μm-pores in their PET membrane was coated with 0.1 mg/ml of collagen. Human umbilical vein endothelial cells (HUVEC) were added to the cell culture inserts (Becton Dickinson) at a density of $5 \times 10^4$ cells/insert. Cells were allowed to migrate through the insert for 18 h in presence of different concentrations of either DTIC or Compound 6. The control culture containing migration assembly received only 0.1% DMSO. The cells which did not migrate were scrapped off by cotton plug and the migrated cells were fixed with methanol for 5 min and then stained with Giemsa. The membranes of the inserts were then mounted on glass slides. Cells migrated through the membrane pores were counted in 20 random fields under Nikon Eclipse TS 100 microscope at 20× objective. FIG. 8 shows significant inhibition of migration of Compound 6 treated endothelial cells.

Example 31

In Vitro Capillary Formation Assay

In vitro capillary formation assay was performed with Human umbilical vein endothelial cells (HUVEC), cultured on 10 mg/ml basement membrane extract (BME-Cultrex®, R&D Systems, USA) bed. The protocol of in vitro endothelial tube formation assay was the same as described earlier with some modifications (44). Briefly, four hundred microliters of Cultrex was coated at 4° C. in each well of 24-well culture plate and allowed to gel at 37° C. for 1 h. HUVECs were plated at a density of $7.5 \times 10^4$ cells per well with 40 μl of DMEM supplemented with 10% fetal bovine serum and 4.5 g/l D-glucose. The cells were then treated with either DTIC or Compound 6 at desired concentration as indicated for 16 hours. Vehicle control cultures received only 0.1% DMSO. Pictures were taken under a Nikon Eclipse TS 100 microscope equipped with a Nikon Coolpix camera. Compound 6 exhibited inhibition of capillary formation in a dose dependent manner, in contrast, DTIC promoted capillary formation with human endothelial cells in in vitro culture condition (FIG. 9).

Example 32

Anti Tumor Growth Potential of Compound 6 in B16 F0 Melanoma Xenograft Model of C57B6J Mice In vivo efficacy of compound 6 against melanoma growth was evaluated in B16 F0 melanoma xenograft model of C57B6J mice (45). C57B6J mice of 6 weeks age (body weight 18-22 g) were purchased from National Institute of Nutrition (NIN), Hyderabad (India). Animals study protocols were approved by Institutional Ethics Committee (IAEC). All the studies were performed in compliance with the Committee for the Purpose of Control and Supervision of Experiments on Animals (CPCSEA) guidelines and OECD guidelines. Animals were allowed free access to standard feed and provided charcoal filtered and UV exposed water ad libitum. The animals were maintained at a controlled temperature (24-26° C.), humidity (45-70%), and 12 h/12 h of light/dark cycle.

To induce the melanoma tumor formation, sub-confluent B16F0 cells were harvested by brief trypsinization and $1 \times 10^6$ cells were injected subcutaneously in 0.2 ml phosphate-buffered saline. Drug treatment was started after development of palpable tumors (3-5 days after implantation of the cells). Drugs were prepared in phosphate-buffered saline (10% DMSO, v/v) and different doses of either DTIC or compound 6 were administered daily through intra-peritoneal route. Vehicle treated control animals received only 10% DMSO. After fourteen days of treatment, the animals were sacrificed by $CO_2$ inhalation and tumors were excised and weighed. FIG. 10 shows comparative efficacy of inhibiting tumor growth by DTIC and compound 6 at various concentrations in B16 F0 melanoma xenograft model of C57B6J mice.

The invention claimed is:

1. A compound of formula (I) or a pharmaceutically acceptable salt thereof:

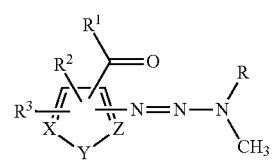

I wherein,
R is selected from the group consisting of H, $CH_3$, and $CH_2OH$;
$R^1$ is selected from the group consisting of OH, $NHR^4$, $NR^4R^5$, and SH;

R² and R³ are independently selected from the group consisting of H, N=N—N(CH₃)₂, N=N—NHCH₃, N=N—N(CH₃)CH₂OH, CONHR⁴, CONR⁴R⁵, CONHNH₂, CONHNHR⁴, CONHNR⁴R⁵, COOCH₃, COOCH₂CH₃, COOH, COSH, CN, C≡CH, SO₂NH₂, SO₂NHR⁴, SO₂NR⁴R⁵, SO₃H, SO₂CH₃, SO₂CH₂CH₂NH₂, NHCH₂COOH, NHCH(CH₃)COOH, NO₂, CF₃, Cl, Br, F, I, CCl₃, Ph (C₆₅), CH₃, C₂H₅, n-C₃H₇, iso-C₃H₇, n-C₄H₉, iso-C₄H₉, tert-C₄H₉, OH, OCH₃, NH₂, and NHCH₃;

R⁴ and R⁵ are independently selected from the group consisting of H, C₁-C₁₀ alkyl, alkenyl, alkylol, and alkylamine; and X, Y, and Z are independently selected from the group consisting of C, N, O, and S, with the proviso that the resulting five membered ring is a substituted or unsubstituted ring selected from the group consisting of thiophene, furan, thiazole, isothiazole, and furazole.

2. The compound of claim 1, wherein said compound is selected from the group consisting of:
3-[(Dimethylamino)diazenyl]thiophene-2-carboxamide;
3-[(Dimethylamino)diazenyl]4-bromothiophene-2-carboxamide;
3-[(Dimethylamino)diazenyl]5-nitrothiophene-2-carboxamide;
4-[(Dimethylamino)diazenyl]3-methoxythiophene-2,5-dicarboxamide;
3-[(Dimethylamino)diazenyl]5-phenylthiophene-2-carboxamide;
3-[(Dimethylamino)diazenyl]thiophene-2-carboxylic acid;
3-[(Dimethylamino)diazenyl]5-nitrothiophene-2-carboxylic acid;
3-[(Dimethylamino)diazenyl]5-phenylthiophene-2-carboxylic acid;
{3-[(Dimethylamino)diazenyl](2-thienyl)}-N-(2-hydroxyethyl)-carboxamide;
{3-[(Dimethylamino)diazenyl](2-thienyl))}-N-methyl-carboxamide;
N-(2-Aminoethyl){3-[(dimethylamino)diazenyl](2-thienyl)}-carboxamide;
4-[(Dimethylamino)diazenyl]thiophene-2-carboxamide;
4-[(Dimethylamino)diazenyl]thiophene-3-carboxamide; and
Potassium salt of 3-[(dimethylamino)diazenyl]thiophene-2carboxylic acid.

3. A compound of formula (II) or a pharmaceutically acceptable salt thereof:

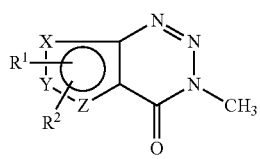

wherein,
R¹ and R² are independently selected from the group consisting of H, N=N—N(CH₃)₂, N=N—NHCH₃, N=N—N(CH₃)CH₂OH, CONH₂, CONHR⁴, CONRR⁴R⁵, CONHNH₂, CONHNHR⁴, CONHNR⁴R⁵, COOCH₃, COOCH₂CH₃, COOH, COSH, CN, C≡CH, SO₂NH₂, SO₂NHR⁴, SO₂NR⁴R⁵, SO₃H, SO₂CH₃, SO₂CH₂CH₂NH₂, NHCH₂COOH, NHCH(CH₃)COOH, NO₂, CF₃, Cl, Br, F, I, CCl₃, C₂H₅, n-C₃H₇, iso-C₃H₇, n-C₄H₉, iso-C₄H₉, tert-C₄H₉, OH, OCH₃, NH₂, and NHCH₃;

R⁴ and R⁵ are independently selected from the group consisting of H, C₁-C₁₀ alkyl, alkenyl, alkylol, and alkylamine; and X, Y, and Z are independently selected from the group consisting of C, N, O, and S, with the provisos that (a) the heterocyclic aromatic five membered ring is a substituted or unsubstituted ring selected from the group consisting of thiophene, furan, thiazole, isothiazole, and furazole; and (b) the compound of general formula (II) is not 3-methylthiopheno[3,2-d]1,2,3-triazin-4-one ((X=Y=C; Z=S; R¹=R²=H).

4. A compound selected from the group consisting of:
3-Methylthiopheno[2,3-d]1,2,3-triazin-4-one;
3-Methyl-6-nitrothiopheno[2,3-d]1,2,3-triazin-4-one;
6-Amino-3-methylthiopheno[2,3-d]1,2,3-triazin-4-one; and
3-Methyl-6-phenylthiopheno[3,2-d]1,2,3-triazin-4-one.

5. A pharmaceutical composition comprising at least one compound of formula (I) as claimed in claim 1 or a pharmaceutically acceptable salt thereof, and a pharmaceutically acceptable diluent or carrier.

6. A pharmaceutical composition comprising at least one compound of formula (I) as claimed in claim 1 or a pharmaceutically acceptable salt thereof, and at least one chemotherapeutic agent and optionally a pharmaceutically acceptable diluent or carrier.

7. The pharmaceutical composition as claimed in claim 6, wherein said chemotherapeutic agent is selected from the group consisting of dacarbazine (DTIC), temozolamide, methotrexate, doxorubicin, cytoxan, 5-fluorouracil, cis-platin, carboplatin, oxaliplatin, vincristine, vinblastine, etoposide, irinotecan, topotecan, paclitaxel, docetaxel, taxotere, taxol, tamoxifen, gefitinib, adriamycin, gemcitabine, melphalan, streptozocin, floxuridine, 6-mercaptopurine, bleomycin, daunorubicin, Mitomycin-C, amsacrine, procabazine, capecitabine, avastin, herceptin, bexxar, velcade, zevalin, xeloda, erbitux (cetuximab), rituximab, and campath (Alemtuzumab).

8. A pharmaceutical composition comprising at least one compound of formula (I) as claimed in claim 1 or a pharmaceutically acceptable salt thereof, optionally at least one chemotherapeutic agent, at least one agent selected from the group consisting of monoclonal antibodies, interferons, interleukins, colony stimulating factors, and TNF-αreceptor blocker drugs, and optionally a pharmaceutically acceptable diluent or carrier.

9. The pharmaceutical composition as claimed in claim 8, wherein said agent is selected from the group consisting of interferon-y; an interleukin selected from the group consisting of IL-1, IL-2, IL-9, IL-11, and IL-12;
and a colony stimulating factor selected from the group consisting of CSF, GM-CSF, and G-CSF.

10. A method for inhibiting cancer cell growth in a patient, wherein said method comprises administering to said patient a compound of formula (I) of claim 1;
wherein said patient has a cancer disease selected from the group consisting of melanoma, breast cancer, prostate cancer, pancreatic cancer, and endothelial cancers.

11. A pharmaceutical composition comprising:
at least one compound of formula (II) as claimed in claim 3 or a pharmaceutically acceptable salt thereof;
and a pharmaceutically acceptable diluent or carrier.

12. A pharmaceutical composition comprising:
   at least one compound of formula (II) as claimed in claim 3 or a pharmaceutically acceptable salt thereof;
   at least one chemotherapeutic agent; and, optionally,
   a pharmaceutically acceptable diluent or carrier.

13. The pharmaceutical composition as claimed in claim 12, wherein said chemotherapeutic agent is selected from the group consisting of dacarbazine (DTIC), temozolamide, methotrexate, doxorubicin, cytoxan, 5-fluorouracil, cis-platin, carboplatin, oxaliplatin, vincristine, vinblastine, etoposide, irinotecan, topotecan, paclitaxel, docetaxel, taxotere, taxol, tamoxifen, gefitinib, adriamycin, gemcitabine, melphalan, streptozocin, floxuridine, 6-mercaptopurine, bleomycin, daunorubicin, Mitomycin-C, amsacrine, procabazine, capecitabine, avastin, herceptin, bexxar, velcade, zevalin, xeloda, erbitux (cetuximab), rituximab, and campath (Alemtuzumab).

14. A pharmaceutical composition comprising at least one compound of formula (II) as claimed in claim 3 or a pharmaceutically acceptable salt thereof, optionally at least one chemotherapeutic agent, at least one agent selected from the group consisting of monoclonal antibodies, interferons, interleukins, colony stimulating factors, and TNF-α receptor blocker drugs, and optionally a pharmaceutically acceptable diluent or carrier.

15. The pharmaceutical composition as claimed in claim 14, wherein said agent is selected from the group consisting of interferon-y;
   an interleukin selected from the group consisting of IL-1, IL-2, IL-9, IL-11, and IL-12; and a colony stimulating factor selected from the group consisting of CSF, GM-CSF, and G-CSF.

16. A method for inhibiting cancer cell growth in a patient, wherein said method comprises administering to said patient a compound of claim 2;
   wherein said patient has a cancer disease selected from the group consisting of melanoma, breast cancer, prostate cancer, pancreatic cancer, and endothelial cancers.

17. A method for inhibiting cancer cell growth in a patient, wherein said method comprises administering to said patient a compound of formula (II) of claim 3;
   wherein said patient has a cancer disease selected from the group consisting of melanoma, breast cancer, prostate cancer, pancreatic cancer, and endothelial cancers.

18. A method for inhibiting cancer cell growth in a patient, wherein said method comprises administering to said patient a compound of claim 4;
   wherein said patient has a cancer disease selected from the group consisting of melanoma, breast cancer, prostate cancer, pancreatic cancer, and endothelial cancers.

19. The method of claim 10, wherein said administering comprises administering by intraperitoneal administration (IP), intravenous administration (IV), oral administration (PO), intramuscular administration (IM), intracutaneous administration (IC), intradermal administration (ID), intrauterine administration, or intrarectal administration.

20. The method of claim 17, wherein said administering comprises administering by intraperitoneal administration (IP), intravenous administration (IV), oral administration (PO), intramuscular administration (IM), intracutaneous administration (IC), intradermal administration (ID), intrauterine administration, or intrarectal administration.

21. The method of claim 10, wherein said administering comprises administering the compound of formula (I) using nanoparticles of different sizes in an emulsion.

22. The method of claim 17, wherein said administering comprises administering the compound of formula (II) using nanoparticles of different sizes in an emulsion.

23. A pharmaceutical composition according to claim 5, further comprising:
   a compound of formula (II) or a pharmaceutically acceptable salt thereof:

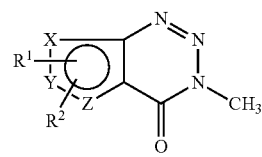

wherein,
   $R^1$ and $R^2$ are independently selected from the group consisting of H, N=N—N(CH$_3$)$_2$, N=N—NHCH$_3$, N=N—N(CH$_3$)CH$_2$OH, CONH$_2$, CONHR$^4$, CONR$^4$R$^5$, CONHNH$_2$, CONHNHR$^4$, CONHNR$^4$R$^5$, COOCH$_3$, COOCH$_2$CH$_3$, COOH, COSH, CN, C≡CH, SO$_2$NH$_2$, SO$_2$NHR$^4$, SO$_2$NR$^4$R$^5$, SO$_3$H, SO$_2$CH$_3$, SO$_2$CH$_2$CH$_2$NH$_2$, NHCH$_2$COOH, NHCH(CH$_3$)COOH, NO$_2$, CF$_3$, Cl, Br, F, I, CCl$_3$, Ph (C$_6$H$_5$), CH$_3$, C$_2$H$_5$, n-C$_3$H$_7$, iso-C$_3$H$_7$, n-C$_4$H$_9$, iso-C$_4$H$_9$, tert-C$_4$H$_9$, OH, OCH$_3$, NH$_2$, and NHCH$_3$;
   $R^4$ and $R^5$ are independently selected from the group consisting of H, C$_1$-C$_{10}$ alkyl, alkenyl, alkylol, and alkylamine; and
   X, Y, and Z are independently selected from the group consisting of C, N, O, and S, with the provisos that (a) the heterocyclic aromatic five membered ring is a substituted or unsubstituted ring selected from the group consisting of thiophene, furan, thiazole, isothiazole, and furazole; and (b) the compound of formula (II) is not 3-methylthiopheno[3,2-d]1,2,3-triazin-4-one ((X=Y=C; Z=S; R$^1$=R$^2$=H).

24. A pharmaceutical composition according to claim 6, further comprising:
   a compound of formula (II) or a pharmaceutically acceptable salt thereof:

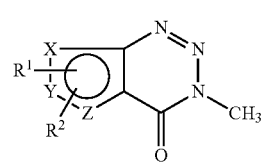

wherein,
   $R^1$ and $R^2$ are independently selected from the group consisting of H, N=N—N(CH$_3$)$_2$, N=N—NHCH$_3$, N=N—N(CH$_3$)CH$_2$OH, CONH$_2$, CONHR$^4$, CONR$^4$R$^5$, CONHNH$_2$, CONHNHR$^4$, CONHNR$^4$R$^5$, COOCH$_3$, COOCH$_2$CH$_3$, COOH, COSH, CN, C≡CH, SO$_2$NH$_2$, SO$_2$NHR$^4$, SO$_2$NR$^4$R$^5$, SO$_3$H, SO$_2$CH$_3$, SO$_2$CH$_2$CH$_2$NH$_2$, NHCH$_2$COOH, NHCH(CH$_3$)COOH, NO$_2$, CF$_3$, Cl, Br, F, I, CCl$_3$, Ph (C$_6$H$_5$), CH$_3$, C$_2$H$_5$, n-C$_3$H$_7$, iso-C$_3$H$_7$, n-C$_4$H$_9$, iso-C$_4$H$_9$, tert-C$_4$H$_9$, OH, OCH$_3$, NH$_2$, and NHCH$_3$;
   $R^4$ and $R^5$ are independently selected from the group consisting of H, C$_1$-C$_{10}$ alkyl, alkenyl, alkylol, and alkylamine; and X, Y, and Z are independently selected from the group consisting of C, N, O, and S, with the provisos that (a) the heterocyclic aromatic five membered ring is a substituted or unsubstituted ring selected from the group consisting of thiophene, furan, thiazole, isothiazole, and furazole; and (b) the compound of formula (II) is not 3-methylthiopheno[3,2-d]1,2,3-triazin-4-one ((X=Y=C; Z=S; $R^1$=$R^2$=H).

25. A compound of formula (II) or a pharmaceutically acceptable salt thereof:

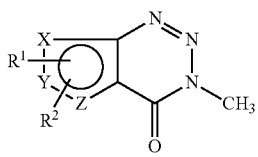

II wherein, $R^1$ and $R^2$ are independently selected from the group consisting of H, N=N—N(CH$_3$)$_2$, N=N—NHCH$_3$, N=N—N(CH$_3$)CH$_2$OH, CONH$_2$, CONHR$^4$, CONR$^4$R$^5$, CONHNH$_2$, CONHNHR$^4$, CONHNR$^4$R$^5$, COOCH$_3$, COOCH$_2$CH$_3$, COOH, COSH, CN, C≡CH, SO$_2$NH$_2$, SO$_2$NHR$^4$, SO$_2$NR$^4$R$^5$, SO$_3$H, SO$_2$CH$_3$, SO$_2$CH$_2$CH$_2$NH$_2$, NHCH$_2$COOH, NHCH(CH$_3$)COOH, NO$_2$, CF$_3$, Cl, Br, F, I, CCl$_3$, Ph (C$_6$H$_5$), CH$_3$, C$_2$H$_5$, n-C$_3$H$_7$, iso-C$_3$H$_7$, n-C$_4$H$_9$, tert-C$_4$H$_9$, OH, OCH$_3$, NH$_2$, and NHCH$_3$;

$R^4$ and $R^5$ are independently selected from the group consisting of H, C$_1$-C$_{10}$ alkyl, alkenyl, alkylol, and alkylamine; and X, Y, and Z are independently selected from the group consisting of C, N, O, and S, with the provisos that:
(a) either:
  i) the heterocyclic aromatic five membered ring is a substituted or unsubstituted ring selected from the group consisting of furan, thiazole, isothiazole, and furazole; or
  ii) the heterocyclic aromatic five membered ring is fused to the heterocyclic six membered ring to form a substituted or unsubstituted thiopheno[3,2-d]1,2,3-triazin-4-one ring system; and
(b) the compound of general formula (II) is not 3-methylthiopheno[3,2-d]1,2,3-triazin-4-one ((X=Y=C; Z=S; $R^1$=$R^2$=H).

26. A pharmaceutical composition comprising:
i) at least one compound of formula (II) as claimed in claim 25 or a pharmaceutically acceptable salt thereof; and
ii) at least one chemotherapeutic agent, at least one pharmaceutically acceptable diluent or carrier, or a mixture thereof.

27. A method for killing cancer cells, wherein said method comprises treating said cancer cells with a compound of formula (I) of claim 1;
wherein said cancer cells are selected from the group consisting of melanoma cancer cells, breast cancer cells, prostate cancer cells, pancreatic cancer cells, and endothelial cancer cells.

28. A method for killing cancer cells, wherein said method comprises treating said cancer cells with a compound of claim 2;
wherein said cancer cells are selected from the group consisting of melanoma cancer cells, breast cancer cells, prostate cancer cells, pancreatic cancer cells, and endothelial cancer cells.

29. A method for killing cancer cells, wherein said method comprises treating said cancer cells with a compound of formula (II) of claim 3;
wherein said cancer cells are selected from the group consisting of melanoma cancer cells, breast cancer cells, prostate cancer cells, pancreatic cancer cells, and endothelial cancer cells.

30. A method for killing cancer cells, wherein said method comprises treating said cancer cells with a compound of claim 4;
wherein said cancer cells are selected from the group consisting of melanoma cancer cells, breast cancer cells, prostate cancer cells, pancreatic cancer cells, and endothelial cancer cells.

31. The method of claim 27, wherein said treating occurs in vitro or in vivo.

32. The method of claim 29, wherein said treating occurs in vitro or in vivo.

* * * * *

UNITED STATES PATENT AND TRADEMARK OFFICE
CERTIFICATE OF CORRECTION

PATENT NO.        : 8,258,119 B2
APPLICATION NO.   : 12/559811
DATED             : September 4, 2012
INVENTOR(S)       : Ganga Raju Gokaraju et al.

Page 1 of 1

It is certified that error appears in the above-identified patent and that said Letters Patent is hereby corrected as shown below:

Col. 43, line 12, change "C1-C10alkyl" to "C1-C10 alkyl".

Col. 43, claim 2, lines 4-5, change "3-[(Dimethylamino)diazenyl]4-bromothiophene-2-carboxamide" to "3-[(Dimethylamino)diazenyl]-4-bromothiophene-2-carboxamide".

Col. 43, claim 2, lines 6-7, change "3-[(Dimethylamino)diazenyl]5-nitrothiophene-2-carboxamide" to "3-[(Dimethylamino)diazenyl]-5-nitrothiophene-2-carboxamide".

Col. 43, claim 2, lines 8-9, change "4-[(Dimethylamino)diazenyl]3-methoxythiophene-2,5-dicarboxamide" to "4-[(Dimethylamino)diazenyl]-3-methoxythiophene-2,5-dicarboxamide".

Col. 43, claim 2, lines 10-11, change "3-[(Dimethylamino)diazenyl]5-phenylthiophene-2-carboxamide" to "3-[(Dimethylamino)diazenyl]-5-phenylthiophene-2-carboxamide".

Col. 43, claim 2, lines 14-15, change "3-[(Dimethylamino)diazenyl]5-nitrothiophene-2-carboxylic acid" to "3-[(Dimethylamino)diazenyl]-5-nitrothiophene-2-carboxylic acid".

Col. 43, claim 2, lines 16-17, change "3-[(Dimethylamino)diazenyl]5-phenylthiophene-2-carboxylic acid" to "3-[(Dimethylamino)diazenyl]-5-phenylthiophene-2-carboxylic acid".

Col. 43, claim 2, lines 27-28, change "3-[(dimethylamino)diazenyl]thiophene-2carboxylic acid" to "3-[(dimethylamino)diazenyl]thiophene-2-carboxylic acid".

Col. 44, claim 9, line 3, change "interferon-y" to "interferon-gamma".

Signed and Sealed this
Twelfth Day of February, 2013

Teresa Stanek Rea
*Acting Director of the United States Patent and Trademark Office*